United States Patent [19]

Wason

[11] 4,336,245

[45] Jun. 22, 1982

[54] NOVEL PRECIPITATED SILICEOUS PRODUCTS AND METHODS FOR THEIR USE AND PRODUCTION

[75] Inventor: Satish K. Wason, Havre de Grace, Md.

[73] Assignee: J. M. Huber Corporation, Locust, N.J.

[21] Appl. No.: 39,061

[22] Filed: May 11, 1979

Related U.S. Application Data

[63] Continuation of Ser. No. 876,284, Feb. 9, 1978, abandoned, which is a continuation of Ser. No. 557,707, Mar. 12, 1975, abandoned.

[51] Int. Cl.$^3$ ............................................. A61K 7/16
[52] U.S. Cl. ..................................................... 424/49
[58] Field of Search .................................. 424/49–58; 423/339; 106/288 B

[56] References Cited

U.S. PATENT DOCUMENTS

| | | | |
|---|---|---|---|
| 3,538,230 | 11/1970 | Pader et al. | 424/50 |
| 3,551,559 | 12/1970 | Miles | 424/49 |
| 3,689,637 | 9/1972 | Pader | 424/52 |
| 3,705,940 | 12/1972 | Kirchgassner | 424/49 |
| 3,711,604 | 1/1973 | Colodney et al. | 424/52 |
| 3,803,301 | 4/1974 | Cordon et al. | 424/49 |
| 3,836,641 | 9/1974 | Hoyles et al. | 424/49 |
| 3,840,657 | 10/1974 | Norfleet | 424/49 |
| 3,842,167 | 10/1974 | Block et al. | 424/49 |
| 3,864,470 | 2/1975 | Watson | 424/49 |
| 3,893,840 | 7/1975 | Wason | 106/288 B |
| 3,893,840 | 7/1975 | Wason | 106/288 B |
| 3,906,090 | 9/1975 | Colodney | 424/52 |
| 3,911,102 | 10/1975 | Harrison | 424/49 |
| 3,911,104 | 10/1975 | Harrison | 424/52 |
| 3,928,541 | 12/1975 | Wason | 423/339 |
| 3,928,541 | 12/1975 | Wason | 423/339 |
| 3,929,987 | 12/1975 | Colodney et al. | 424/52 |
| 3,934,000 | 1/1976 | Barth | 424/49 |
| 3,935,306 | 1/1976 | Roberts et al. | 424/49 |
| 3,939,262 | 2/1976 | Kim | 424/52 |
| 3,960,586 | 6/1976 | Wason | 106/288 B |
| 3,967,563 | 7/1976 | Wason | 106/288 B |
| 3,977,893 | 8/1976 | Wason | 106/288 B |
| 3,988,161 | 10/1976 | Wason | 106/288 B |
| 3,993,497 | 11/1976 | Wason | 106/288 B |
| 4,015,996 | 4/1977 | Wason | 106/288 |
| 4,038,098 | 7/1977 | Wason | 106/288 B |
| 4,040,858 | 8/1977 | Wason | 106/288 B |
| 4,045,240 | 8/1977 | Wason et al. | 106/288 B |
| 4,067,746 | 1/1978 | Wason et al. | 106/288 B |
| 4,076,549 | 2/1978 | Wason | 106/288 B |
| 4,105,757 | 8/1978 | Wason | 424/49 |
| 4,122,160 | 10/1978 | Wason | 424/49 |
| 4,122,161 | 10/1978 | Wason | 424/49 |
| 4,140,757 | 2/1979 | Wason et al. | 424/49 |
| 4,144,321 | 3/1979 | Wason | 424/49 |
| 4,156,717 | 5/1979 | Wason | 424/49 |
| 4,157,920 | 6/1979 | Wason et al. | 106/292 |
| 4,161,455 | 7/1979 | Wason | 252/174.2 |

Primary Examiner—Shep K. Rose
Attorney, Agent, or Firm—Robert L. Price; Harold H. Flanders

[57] ABSTRACT

A method for producing a precipitated silicon dioxide having a new combination of physical and chemical properties is disclosed. The pigments are produced by acidulating a solution of an alkali metal silicate with an acid under controlled precipitation conditions. The aqueous reaction medium comprising the precipitated silica is then post-conditioned by introducing a second silicate solution into the reaction vessel and thereafter adding additional acid to react with the said second silicate solution. By varying the amount of the silicate employed in the post-conditioning step, a product is obtained which has a unique combination of physical and chemical properties including reduced wet cake moisture content, high surface areas and oil absorptions, improved surface activity, friability, wetting characteristics, and the like. The product has particular utility for use as a rubber reinforcing agent because of its increased surface activity and oil absorption, etc. The product, however, may be used in paints, paper, detergents, dentifrice compositions, molecular sieves, and polymeric compositions. An unexpected discovery of the invention involves the production of a rubber reinforcing silica which has a decreased wet cake moisture content. In one particularly advantageous embodiment, an adduct material, such as aluminum, is added to control the refractive index and surface area of the product.

12 Claims, 16 Drawing Figures

1μ÷10
192,000x

1μ→10
69,800×

1μ ÷ 10
69,800X

1μ ÷ 10
192,000x $1\mu \div 10$
69,800X

NOVEL PRECIPITATED SILICEOUS PRODUCTS AND METHODS FOR THEIR USE AND PRODUCTION

This is a continuation of application Ser. No. 876,284, filed Feb. 9, 1978 which is a continuation of Ser. No. 557,707, filed Mar. 12, 1975, both now abandoned.

BACKGROUND OF THE INVENTION

1. Field of the Invention

The present invention relates to novel synthetic precipitated silicas and to a process for producing a synthetic precipitated silicon dioxide having a new and improved combination of properties and characteristics. More particularly, the invention relates to the production of precipitated high structure silicas produced by reacting aqueous alkali metal silicate solutions with an acidification agent. The novel products are high structure finely divided silicas having certain unique properties particularly with respect to structure index, oil absorption, void volume, surface activity, friability, wetting characteristics, and further properties. The novel products are especially suitable for use as reinforcing agents in rubber, in paints, paper, detergents, molecular sieves, and in polymeric compositions.

2. Description of the Prior Art

As known in the art, finely divided silica or silicon dioxide particulates can be prepared by the acidulation of an aqueous silicate solution with an acid, such as sulfuric acid. Such products are commercially available and are characterized by, and have, the following properties: high structure, high wet cake moisture content, high oil absorption, low valley abrasion, high surface area, and low pack density. Because of properties such as high oil absorption, the pigments have been successfully used as reinforcing pigments in rubber. However, the high wet cake moisture content is disadvantageous in that the drying and filtration rates are increased. Further, the aforementioned properties of said known and commercially available silicas render them unsuitable for many uses.

In this regard and generally speaking for the moment, known processes including those described in the literature as well as those techniques employed in the industry produce products suitable for use as reinforcing fillers. Thus, in U.S. Pat. No. 2,940,830 which issued June 14, 1960 to F. S. Thornhill, there is described a process for preparing finely divided silicas which are suitable as reinforcing agents in rubber compositions. Thornhill more specifically describes a process of preparing a silica material which is characterized by having an average ultimate particle size of 0.015 to 0.04 micron and a surface area of 25 to 200 square meters per gram by the controlled rate of addition of acid to an alkali metal silicate wherein the resultant slurry is constantly maintained at a pH above 7 in order to achieve the aforementioned end-product characteristics. The Thornhill patent is specifically directed to the production of a product suitable as a reinforcing agent in rubber compositions.

In U.S. Pat. No. 3,235,331, which issued Feb. 15, 1966 to Nauroth et al., there is described a process for producing a precipitated silica which is also stated to be useful as a reinforcing agent for rubber. More specifically, this patent discloses a process wherein an aqueous alkali metal silicate solution and acid are simultaneously added to a reaction vessel. In the Nauroth et al. patent, it is pointed out that this simultaneous addition is continued until the viscosity of the pool rises through a maximum and then falls to a substantially lower value. The amount of the acidification agent and the alkali metal silicate are proportioned so as to maintain the pH of the resulting slurry substantially constant throughout the major portion of the reaction and in the range of about 10 to 12. The process is generally conducted at a temperature of 80° to 90° C. and the end product, after drying, results in a silica which may have a surface area of 260 square meters per gram. The patentees point out that the product is satisfactory as a reinforcing agent for rubber.

In U.S. Pat. No. 3,445,189 issued May 20, 1969 to Maat et al., there is described a process for producing finely divided silicic acid by simultaneously adding solutions of an alkali silicate and a strong mineral acid to water at a temperature between 70° C. and 90° C. while maintaining the reaction pH between 7 and 9. The patentees point out that the product obtained by the aforementioned process is a finely divided non-gelatinous silicic acid which is useful as a filler for natural and synthetic rubber and other elastomers. It is also disclosed in this patent that for a silica to be useful as a filler for natural and synthetic rubber and other elastomers, its surface area and oil absorption are of vital importance. This patent further discloses that extensive investigation have further indicated that if a finely divided silicic acid is to have good reinforcing properties for rubber, it must have a surface area of 100 to 250 $m^2/g$ and an oil absorption of more than 2 cc/g or 200 cc/100 g. See column 2, lines 18 through 22.

In U.S. Pat. No. 3,730,749, which issued May 1, 1973 to James E. Morgan, there is disclosed a process for preparing silica for use in reinforcing compositions. It is pointed out in Morgan that the viscosity increase which occurs during the acidification or neutralization of aqueous alkali metal silicate is substantially minimized by adding a controlled amount of an alkali metal silicate. In Examples I, II, and III of this patent, it is also noted that the silica filter cakes had solid contents of 18.5; 24.9; and 25.1 percent, respectively. This means that the percent wet cake moisture of the silicas disclosed in Examples I, II, and III is one hundred minus the percent solid content in the filter cake. In other words, the percent wet cake moisture (% WCM) of silicas mentioned in Examples I, II, and III is 81.5; 75.1; and 74.9, respectively. The surface area, the average ultimate particle sizes, and rubber data of silicas produced by the teachings of Examples II and III are listed in Table 3 which also sets forth that rubber compositions incorporating the silicas of Examples II and III have desirable rubber properties. It is further substantiated by this patent that rubber properties of silicas are related to the high wet cake moisture of the silica pigment. Thus, it is taught that a silica of high percent wet cake moisture and suitable particle size and surface area has better rubber properties than the corresponding material of lower wet cake moisture. Thus, the silicas disclosed in Morgan have a higher structure index, and therefore the silicas are useful rubber reinforcing fillers.

From the above it will be seen that the structure index of a silica is related to the rubber properties—a silica of higher structure index will have better rubber properties than a silica of lower structure index. At this point and before turning to the remarkable concept of the present invention, the various types of synthetic silicas, as well as "structure" and "structure index" should therefore be discussed.

In this regard, and as known and accepted in the art, commercially available synthetic silicas are derived either by a liquid phase or a vapor process. Silicas obtained by the vapor process are called fumed or pyrogenic silicas. Products obtained by the liquid process are categorized as silica gels and precipitated silicas. Thus, there are three distinct types of synthetic silicas on the market:

1. Pyrogenic Silicas

Pyrogenic or fumed silicas are prepared by reacting silicon tetrachloride vapor with oxygen and hydrogen gas at high temperatures. These products have high external surface areas and differ from other silicas (e.g., gels, precipitated silicas) prepared from the liquid phase process. Cabot and DeGussa are two suppliers of pyrogenic silicas.

2. Silica Gels

Silica gels are of two types: hydrogels and aerogels. Hydrogels are prepared by reacting a soluble silicate such as sodium silicate with strong sulfuric acid. The gel is washed salt free, dried, steam micronized, and then classified. Aerogels are prepared from crude hydrogels by displacing its water content with an alcohol. The alcohol is then recovered by heating the gel in an autoclave.

Aerogels are lighter and fluffier than hydrogels because the shrinkage of the gel structure is avoided during the drying process. Gels have very large surface areas, generally in the range of 300–1,000 $m^2/g$ and high porosities. Silica gels are offered, e.g., by W. R. Grace and Company under the trademark "Syloid"; by Monsanto, under the trademark "Santocel"; and by Glidden, under the trademark "Silcron."

3. Precipitated Silicas

Precipitated silicas are produced by the de-stabilization and precipitation of silica from soluble silicate by the addition of a mineral acid and/or acidic gases. The reactants thus include an alkali metal silicate and a mineral acid, such as sulfuric acid or an acidulating agent such as $CO_2$.

When the acidification agent is added to the alkali metal silicate at a certain point during the process, the silica starts precipitating. The addition of the acidification agent is continued until the $M_2O$ of the alkali metal silicate (M being the alkali metal) of the ultimate silica is less than about 1% by weight. Thus, as a general rule, the acidification agent is added to the alkali metal silicate to neutralize the alkali portion bound to the silicate anion. The reaction slurry is filtered and washed free of reaction by-product, which is the alkali metal salt of the acidification agent. The filter cake is dried and milled to obtain a silica of desired degree of fineness.

Prior to the drying step the silica filter cake generally results in a filter cake which contains a surprisingly high amount of water. For example, a silica which is useful as a filler for reinforcement of rubber and elastomers generally contains 80% to 85% water in its cake. For example, see Example No. I, U.S. Pat. No. 3,730,749 where the percent wet cake moisture is 81.5. The percent water present in the filter cake is known as percent wet cake moisture or, generally abbreviated as "% WCM." One hundred minus the % WCM gives the solid content of the filter cake, i.e., the amount of silica which can be recovered in the solid form upon drying the filter cake. The percent solid content of the filter cake is termed percent filter cake solids and generally abbreviated as "% FCS." Thus, % WCM and % FCS are related by the equation:

$$\% \ WCM = 100 - \% \ FCS$$

or $$\% \ FCS = 100 - \% \ WCM$$

If we know the value of % WCM, we can calculate % FCS or vice versa.

Thus, a silica filter cake having 85% WCM will have 100 minus 85 or 15% FCS. This means that 15 pounds of silica can be recovered from such a filter cake by evaporating or drying 85 pounds of water from 100 pounds of filter cake. The total weight of filter cake consists of water and solid silica. In the example where the % WCM is 85, one can recover only 15 pounds of solid silica as can be seen below:

100 pounds filter cake = 85 pounds water + 15 pounds dry silica
= 85% WCM + 15% FCS Thus, there are 85 pounds of water associated with 15 pounds of solid silica content or $(85/15) \times 100 = 567$ of water per 100 pounds of solid silica.

The water associated with the silica content of filter cake is structural water. This water is present whereby it occupies the available space between the silica aggregates and also the space inside the silica aggregates. As used herein, the term "structure" is defined as the ability of a silica to hold water in its wet cake. When silicas, such as the aforementioned known prior art products, hold a high percentage of water, i.e., from about 70 to 85%, they are known as high structure silicas. Materials holding less than 70% or from about 50 to 70% are referred to as low structure silicas. This total structural water content is a very important property of silica and is directly related to the functional and end use properties of silica. The amount of total structural water associated with 100 pounds of solid silica content of the filter cake is defined as "structure index" and abbreviated as S. I.

Mathematically, structural index (S. I.) of silica can be calculated if either the % wet cake moisture (WCM) or the % filter cake solid (FCS) values of said silica are known:

$$S.\ I. = (\% \ WCM)/(100 - \% \ WCM) \times 100 = \% \ WCM/\% \ FCS \times 100$$

Structural index of silicas in wet cake moisture range of 80–85% is listed in Table I.

TABLE I

| | Structure Index of Silicas With % WCM of 85-80 | |
|---|---|---|
| % WCM | 100 - % WCM | S. I. |
| 85 | 15 | 567 |
| 84 | 16 | 525 |
| 83 | 17 | 488 |
| 82 | 18 | 455 |
| 81 | 19 | 426 |
| 80 | 20 | 400 |

Prior art precipitated silicas such as disclosed in the aforementioned patents (see U.S. Pat. Nos. 2,940,830; 3,235,331; 3,445,189; 3,730,749) are high structure silicas having high S. I. values. As stated, these silicas are useful as reinforcing fillers in elastomers and rubber. As a final point in this discussion of the prior art, it may be noted that in addition to the aforementioned high structure reinforcing silicas, there has recently been developed a new class of low structure silica compounds which, though unsuitable as reinforcing fillers, have utility for use in specific areas such as polishing and cleaning agents in dentifrices. Specific examples of such new products and methods for their production are disclosed in U.S. patent applications Ser. Nos. 286,655, filed Sept. 6, 1972 (now allowed) and 472,580, filed May 22, 1974.

SUMMARY OF THE INVENTION

In summary, the present invention relates to novel precipitated high structure silicas, to a unique process for producing same and to methods for their use. The present invention is based, in part, on the remarkable discovery that the post-conditioning of suspended finely divided silica particulates, under conditions as described in detail hereinafter, not only affects or significantly alters their properties, but also serves to enhance their properties for a given use, i.e., as rubber reinforcing agents and to render them suitable for use (because of said new properties) in new fields.

In its broadest aspects, in the practice of the method of the instant invention, a known volume of an aqueous solution of an alkali metal silicate is first introduced into a reaction vessel. An acidification agent, such as sulfuric acid, is then added to the silicate solution until finely divided silica or silicon dioxide particulates are precipitated. The amount of the acidification agent added should be that theoretically required to react with the silicate to form, or precipitate, silicon dioxide in accordance with the general formula:

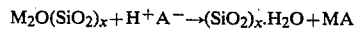

$$M_2O(SiO_2)_x + H^+A^- \rightarrow (SiO_2)_x \cdot H_2O + MA$$

wherein M is an alkali metal, A is an acid salt radical, and x is a number from 1 to 4. During the precipitation, sufficient agitation is provided to insure intimate mixing of the reactants.

As briefly stated above, the present invention embodies the concept and discovery that the properties of the aforesaid precipitated silicon dioxide particulates may be significantly altered and/or tailored to a given end use by introducing a second and known volume of an alkali metal silicate solution into the reaction mass comprising the precipitated silicon dioxide particulates and acidifying the thus added silicate so that, at least to the theory best understood by the inventors, a fine coating of silicone dioxide is formed on the precursor particulates. Finely divided silica products produced in this manner have, depending upon the amount of the post-conditioning, enhanced reinforcing rubber properties and a unique overall combination of properties which render them particularly suitable for use in many areas. In addition, the precipitated silicas have a reduced wet cake moisture content which significantly reduces their overall cost of production. The fact that a product can be produced with improved rubber reinforcing properties, yet have a lower wet cake moisture content, is remarkable and is in direct contrast to the teaching of the prior art. In other words, the findings of the invention are unexpected. In addition, new use areas are made possible because of the aforesaid new properties. Thus, the precipitated pigments produced in accordance with the invention result in silica products which have a unique balance of physical, chemical properties as compared to conventionally known silicas.

It is accordingly a general object of the present invention to provide finely divided silicon dioxide particulates having a new and unique combination of physical and chemical properties.

Other objects are to provide a process for controlling the relative sizes and uniformity of primary and secondary particles of silica for the production of improved silica pigments for various applications; to provide a silica pigment of minimal or no built-in microporosity; to provide a silica pigment of improved surface reactivity, friability, wetting characteristics and generally improved physical/chemical properties; to decrease the structure index and wet cake moisture of silica pigment without corresponding reduction in absorption, without loss of thickening and without loss of viscosity building characteristics of the silica pigment; to provide an improved process to enhance the filtration characteristics of silica pigment; to provide a silica pigment of improved end-use functionality and to provide an improved process for producing silica pigments of equal or better functionality than prior art silicas, but at an economical cost. Further, objects of the present invention are to increase the particle-particle void structure without increasing the overall production cost of silica pigments. Yet another object of the present invention is to provide a process for producing high structure finely divided silicon dioxide by the acidulation of an alkali metal silicate, the improvement comprising post-conditioning the precipitated silica reaction slurry with an alkali metal silicate solution to decrease the structural microporosity. The microporosity is disadvantageous to have for the effective usefulness of the pigmentary silica in rubber compositions. The silicate treatment of the instant process promotes the growth of particles and results in a homogeneous final product of uniform particle size wherein structural microporosity is avoided.

BRIEF DESCRIPTION OF THE DRAWINGS

The manner in which the foregoing and other objects are achieved in accordance with the present invention will be better understood in view of the following detailed description and accompanying drawings, which form a part of the specification and wherein.

DESCRIPTION OF PREFERRED EMBODIMENT(S)

Figure 1:
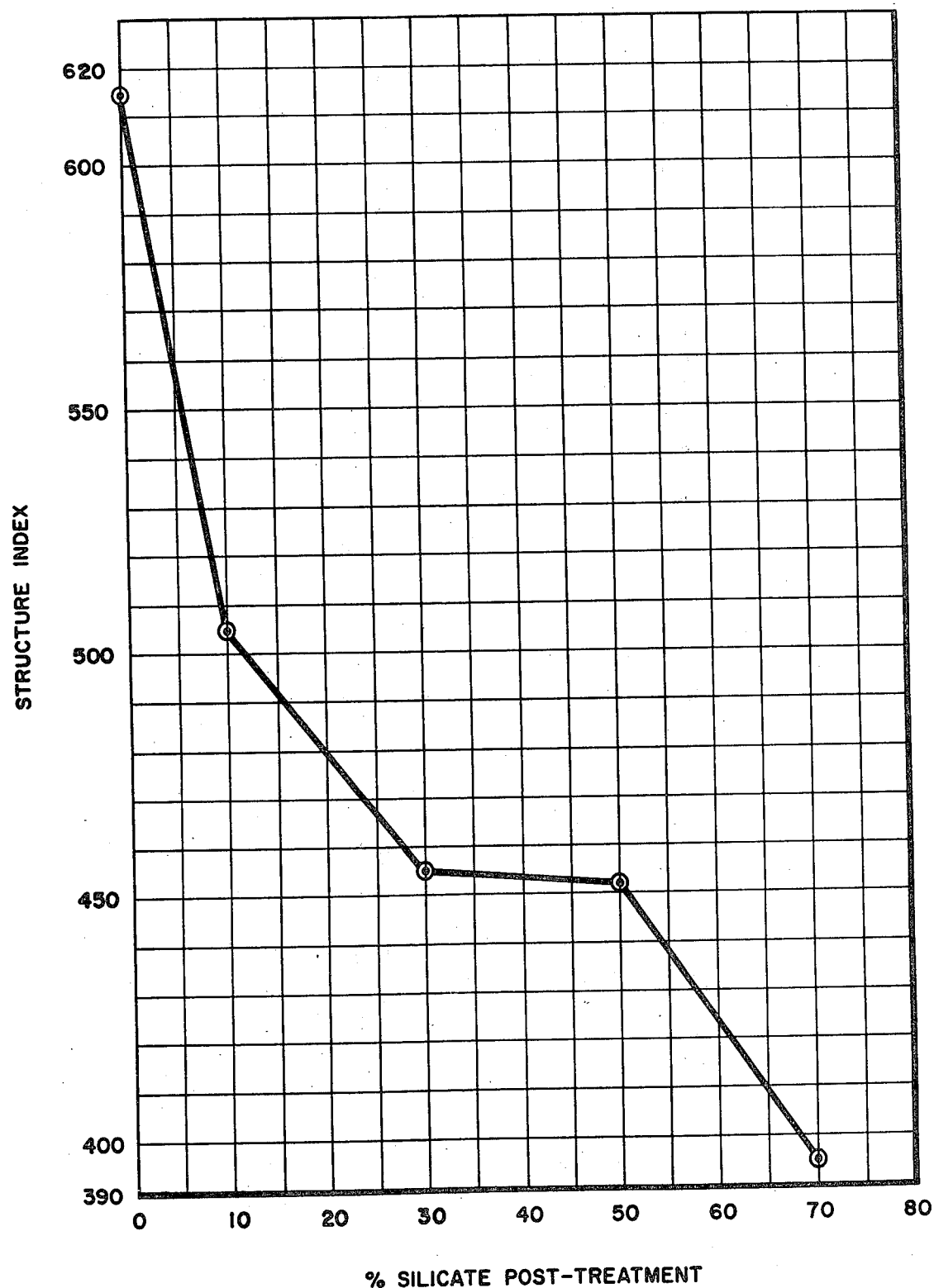
FIG. 1 is a graph illustrating the change in the structure index of silica as a function of silicate post-treatment.

In accordance with the present invention, there is provided an improved process for producing a high structure silica which is useful as a reinforcing agent in rubber and elastomers and, in fact, has improved properties therefor. In the practice of the invention, an alkali metal silicate solution is first acidulated until at least 99% of the silicon dioxide is precipitated. That is, 99% of the alkali portion bound to the silicate anion has been reacted. At this point, the precipitated silica slurry is post-conditioned with calculated amounts of a silicate solution. Acid is then introduced into the reaction medium in an amount theoretically required to react with the second silicate solution added to the precipitated silica slurry. The amount of the silicate solution added in the post-conditioning step will vary depending upon the particular properties desired, but should be from about 10 to 70% by weight of the initial silicate that is acidulated with the acid. Stated differently, the silicate and the acid introduced in the post-conditioning step should be such that it precipitates additional silica, the latter comprising from about 10 to 70% of the silica present in the slurry prior to the said post treatment.

In the prior art, it is generally taught that during the acidulation of alkali metal silicate, a maximum reaction viscosity is observed when the alkali metal silicate is neutralized between about 25 percent and 60 percent (theoretical). It is suggested that the increase in viscosity contributes to the formation of aggregates having a wide range of particle sizes which are unsuitable for use in rubber and paper compositions. It is also generally recognized that due to localized gelation, the proper nucleation of silica micelles does not take place during the periods of high viscosity. This results in and accounts for very high wet cake moisture content of prior art silicas. By the present invention, it is possible to reduce the wet cake moisture of precipitated silicas without sacrificing the beneficial rubber properties. In fact, they are improved. It is also taught that the wet cake moisture and the structure of silica go hand in hand. Thus, it is disclosed that as the wet cake moisture goes up, the rubber properties of a pigment are also improved. The increase in wet cake moisture is related to an increase in production costs. Higher wet cake moisture means that during factory processing, the drying and processing costs of such a silica go up. It is, therefore, of vital importance to reduce the wet cake moisture of a silica pigment while still maintaining substantially high structure index in a silica pigment for it to function as a useful reinforcing pigment. This was not possible prior to the present invention.

Thus, a focal point of the present invention is to provide an improved process for producing a silica pigment which is useful as a rubber reinforcing filler. The improved process results in the reduction of wet cake moisture, yet it does not degrade the rubber reinforcing properties and other utility of silica pigments. This, as stated, is truly unexpected.

In the practice of the present invention, the following process steps are employed.

(1) A known volume of an alkali metal silicate (of known or fixed composition) is charged to the reactor.

(2) The acidification agent is added gradually to the silicate solution until at least 99% of the theoretical amount of the silica is precipitated.

(3) The reaction temperature is maintained between 60° C. to 95° C. throughout the entire process of acidification.

(4) The reaction slurry is conditioned by post-treating the precipitated silica with controlled amounts of alkali metal silicate solution.

(5) An acid is then added in an amount sufficient to react with the silicate introduced in Step (4).

(6) The reaction mass is adjusted to a desired final pH depending on its intended use.

(7) After post-treatment with silicate solution and final pH adjustment, the reaction slurry is filtered, washed free of reaction by-product, dried and may be milled to the desired degree of fineness.

It was unexpectedly discovered that the post-treatment of silica reaction slurry results in significant reduction in the wet cake moisture content of the silica product without corresponding and expected reduction in end-use functionality. In fact, rubber and other properties are improved.

The alkali metal silicate used should normally have the composition $M_2O \, (SiO_2)_X$ where M is an alkali metal and X is 2 or above, usually 2 to 4 including the fractional numbers. Sodium or potassium silicates and other alkali metal silicates can be used, but sodium silicate is preferred because it is most economical to use. Several mineral acids and other weak acidification agents like $CO_2$ and organic acids may be employed in the practice of the invention. Examples of mineral acids which have been found especially suitable include phosphoric, nitric, hydrochloric, and sulfuric acid. Of these, hydrochloric acid and sulfuric acid are preferred and sulfuric acid is particularly preferred because it is the most economical mineral acid to use. If the mineral acid is a dibasic acid, i.e., sulfuric, the concentration of the acid solution should be on the order of 8 to 22% and preferably from about 10 to 15% by weight. Other acids, such as mono or tribasic acids, should have their concentration adjusted to normalities (n) equivalent to the dibasic acid. It is believed that the low mineral acid concentration helps to minimize localized reactions of high concentration of the alkali metal silicate solution.

Turning now to further specific details, in the practice of the invention, the alkali metal silicate is first charged to a reactor as a solution thereof and the solution is heated to a temperature in the range of from about 60° C. to 90° C., preferably on the order of from about 60 to 80° C. with continuous agitation. The concentration of the alkali metal silicate should be in the range of from about 8 to 25% by weight silicate, preferably from about 8 to 15% by weight silicate.

The acidulating agent or acid, e.g., sulfuric acid, is next charged to the reaction vessel until the precipitation is substantially complete, i.e., at least 99% of the theoretical amount of the silica is precipitated. Following precipitation and while maintaining the precipitate in suspension (e.g., by agitation), the slurry or suspension is post-conditioned by first introducing an alkali metal silicate solution having substantially the same concentration as the initial silicate solution. The amount added should comprise from 10 to 70% by weight of that silicate solution initially charged to the reactor. If the concentration of the solution is the same, the amount of the total silicate solution added in the post-treatment will, of course, simply comprise from 10 to 70% of the solution added initially. Acid is then added to react with the second silicate added in the post-treatment step.

The instant invention results in a new class of products having a unique combination of physical and chemical properties. These include the combination of an oil absorption of greater than 190 cc/100 grams and a structure index of 505. In fact, in the practice of the invention one can obtain a product having an oil absorption in the range of from between about 190 to 212 cc/100 grams with a corresponding structure index range of from between about 505 to 350. As will be seen in the following examples, it was found that as the percent post-treatment was increased above 10%, the structure index decreased yet at the same time the oil absorption increased. This was unexpected and the combination of increased oil absorption and reduced wet cake moisture (or structure index) is novel. Further properties of the product of the invention include a surface area in the range of from between about 120 to 220 sq. meters per gram; a void volume of from between about 3.55 to 4.44 ccHg/gram $SiO_2$ and a friability of up to 98%.

In one particularly advantageous embodiment, the refractive index and surface area of the precipitated product is controlled by the addition of an adduct element, such as aluminum, magnesium, and the like. In this regard it may be noted that post-conditioning actually decreases the surface area of the resulting product over that of a control (no treatment). A minimum surface area is obtained at a post-conditioning treatment level of between about 30 to 50%. This reduction in surface area is believed to be due to the elimination of microporosity. However, the adduct not only serves to increase the refractive index, but also increases the surface area of post-conditioned product. In this embodiment, the acid is premixed with a solution of the adduct material, i.e., aluminum (preferably in the form of a water soluble salt thereof, such as aluminum sulfate, etc.) and the acid-metal salt mixture is then used for acidulating the aqueous alkali metal silicate solution. It has been found that the addition of the adduct changes (increases) the surface area and refractive index of the product but does not substantially affect the other properties thereof. Specific metals that may be employed include water soluble salts of aluminum, magnesium, calcium, and zinc.

In the practice of the invention, improved and very important processing advantages are also obtained. While particular embodiments have been disclosed for illustrative purposes, the invention is not intended to be limited thereto. For example, a product can be easily produced for a special utility. Also, and as should be readily appreciated by those skilled in the art, no special equipment is required in the method herein described. In this regard, the reactor or reaction vessel should be equipped with heating means, e.g., a steam jacket, in order to maintain the desired reaction temperature and should have adequate agitation means to produce a strong backflow on the body of the liquid and to avoid zones of high concentration of the incoming reactants. Storage vessels (for the reactants) connected to the reaction vessel through lines fitted with flow control means may also be provided. The reaction vessel may be equipped with an outlet line leading to a filter which may be of conventional design. As noted above, the filtered mass is washed and dried. Such steps may also be conducted in conventional equipment.

The following Examples will serve to further illustrate the present invention, but it should be expressly understood that they are not intended to limit it thereto.

EXAMPLE I

A concentrated sodium silicate solution of 38.2% solids and of composition 10.7% $Na_2O$ and 27.5% $SiO_2$ was diluted with sufficient water to prepare a dilute sodium silicate solution of 3.78% $Na_2O$ and 9.52% $SiO_2$. The specific gravity of this dilute silicate solution was 1.121.

A 93.0% commercial sulfuric acid from the storage tank was diluted with sufficient water to prepare a dilute sulfuric acid solution of 11.4% concentration and of specific gravity 1.076 @ 20° C. These dilute sodium silicate and dilute sulfuric acid solutions were used for preparing silica pigments per following reaction conditions:

| | |
|---|---|
| Sodium Silicate Volume | 37.85 liters |
| Sodium Silicate Composition | 3.78% $Na_2O$ |
| | 9.52% $SiO_2$ |
| Specific Gravity of Dilute Silicate Solution | 1.121 @ 20° C. |
| Dilute Sulfuric Acid Concentration | 11.4% |
| Temperature of Sulfuric Acid | 38° C. |
| Sulfuric Acid Addition Rate | 400 ml/min |
| Reaction Temperature | 80° C. |

PROCEDURE 37.85 liters of sodium silicate solution (of composition 3.78 percent $Na_2O$, 9.52 percent $SiO_2$) was added into a 130 liter stainless steel reactor jacketed for steam heating.

The silicate solution was heated to a reaction temperature of 80° C. Sulfuric acid solution of 11.4% concentration and at 38° C. was added at the rate of 400 ml/min to the reactor maintained at a reaction temperature of 80° C.

The acid addition was continued until a final pH of 5.8–6.0 was obtained. The reaction slurry was boiled at 100° C. for 20 minutes and the final pH was readjusted to 5.8 to 6.0. The resulting slurry contained 8% silica and was filtered on a filter press. The filter cake was washed with water to free it from the reaction by-product (sodium sulfate).

A portion of the filter cake was dried @105° C. until constant weight to determine the percent wet cake moisture and the structure index of silica pigment.

The remainder of the silica was dried in the oven and dry material milled to the desired degree of fineness. The dry fine particulate silica powder was subjected to various physical-chemical tests.

The above-mentioned reaction conditions and procedure are typical of a method by which a conventional prior art precipitated silica is produced. Therefore, this Example I will be compared to support the improved properties of silica obtained by the instant invention.

The prior art silica of Example I was subjected to various tests and the following data was obtained:

| | |
|---|---|
| % Wet Cake Moisture | = 86.0 |
| Structure Index | = 615 |
| Oil Absorption | = 172 cc/100 gram |
| Particle-Particle Void Volume | = 2.95 cc Hg/gram silica |
| BET Surface Area | = 164 square meters per gram |
| Percent Friability | = 10 |

The following procedures were used for calculating the above data.

The structure index (S. I.) was calculated by using the following equation:

$$S.\,I. = (\%\ WCM/100 - \%\ WCM) \times 100$$

The oil absorption of the end product produced from Example I was determined by the rub-out method. This method is based on a principle of mixing linseed oil with a silica by rubbing with a spatula on a smooth surface until a stiff putty-like paste is formed. By measuring the quantity of oil required to give a paste mixture which will curl when spread out, one can calculate the oil absorption value of the silica—a value which represents the volume of oil required per unit weight of silica to saturate the silica sorptive capacity. Calculation of oil absorption value was done as follows:

$$\text{Oil Absorption} = \left( \frac{\text{cc oil absorbed}}{\text{weight of silica, grams}} \right) \times 100$$

$$= \text{cc oil/100 gram silica}$$

The specific surface area of the end product was determined by the nitrogen absorption method described by Brunauer, Emett, and Teller (BET) in the "Journal of the American Chemical Society," Volume 60, page 309, published in 1938.

The particle-particle void volume of silica was determined by using the Aminco-Winslow Porosimeter. This instrument is a completely hydraulic machine used to measure the void structure of various materials. The mercury is forced into the voids as a function of pressure and the volume of mercury displaced per gram of sample is calculated at each pressure setting. Increments in volume (cc/g) at each pressure setting are plotted against the void size increments corresponding to the pressure setting increments. The following data was collected for the prior art, control silica of Example I (see Table IA).

TABLE IA

| Pressure Gage PSIG | Pore Diameter Microns | Cumulative Intruded Volume, cc Hg/g Silica | Intruded Volume, cc Hg/g |
|---|---|---|---|
| | 102 | 0.00 | 0.00 |
| | 51 | 0.05 | 0.05 |
| | 26 | 0.23 | 0.18 |
| 3.3 | 13 | 0.48 | 0.25 |
| 16.3 | 6 | 0.71 | 0.23 |
| 41 | 3 | 0.96 | 0.25 |
| 96 | 1.6 | 1.32 | 0.36 |
| 206 | 0.8 | 1.62 | 0.30 |
| 427 | 0.4 | 1.83 | 0.21 |
| 869 | 0.2 | 2.01 | 0.18 |
| 1750 | 0.1 | 2.18 | 0.17 |
| 3520 | 0.05 | 2.44 | 0.26 |
| 7060 | 0.025 | 2.95 | 0.51 |

The above data (see Table IA) suggests that void sizes between 0.025 microns and 51 microns exist in the prior art control silica of Example I. The total particle-particle volume of the voids is 2.95 cc Hg/gram silica. As will be seen later in Examples II through V that by using the improved process of the instant invention, it is possible to increase the total void volume to values higher than 2.95.

EXAMPLE II

The procedures of Example I were repeated except that the improvement consisted in post-treating the precipitated silica reaction slurry with silicate solution.

In the actual practice of this invention, 37.85 liters of sodium silicate solution (of composition 3.78% $Na_2O$ and 9.52% $SiO_2$) was added into a 130 liter stainless steel reactor jacketed for steam heating.

The silicate solution was heated to a reaction temperature of 80° C. Sulfuric acid of 11.4% concentration at 38° C. was added to the reactor at the rate of 400 ml/min. The reaction temperature was maintained constant at 80° C.

The acid addition was continued until substantially all the silica was precipitated. The precipitated reaction slurry at pH 7 was post-treated with silicate solution. The treatment level corresponded to 10% by weight of the precipitated silica in the reaction slurry.

In the actual practice of the invention, the reaction slurry containing the precipitated silica at a neutral pH was post-treated by adding 3.785 liters of sodium silicate solution in five minutes. The post-treatment increased the pH of the reaction medium. Additional sulfuric acid was added to bring the final pH of the reaction slurry below 6.0. The resulting slurry was boiled at 100° C. for 20 minutes and filtered on a filter press. The filter cake was washed with water to free it from the reaction by-product (sodium sulfate).

A portion of the filter cake was dried at 105° C. until constant weight to determine the percent wet cake moisture and the structure index of the silica product.

The remainder of the silica was dried in the oven and dry material milled to the desired degree of fineness. The dry, fine particulate silica powder was tested for various physical and chemical properties and the following data was obtained:

| | |
|---|---|
| % Wet Cake Moisture | 83.5 |
| Structure Index | 505 |
| Oil Absorption | 190 cc/100 gram |
| Particle-Particle Void Volume | 3.55 cc Hg/g silica |
| BET Surface Area | 141 m²/g |
| Percent Friability | 20 |

Examining the above data and comparing with Example I, it will become clear that the post-treatment of the precipitated silica slurry results in higher void volume, higher oil absorption, better friability, lower structure index and lower surface area than the control (see Example I).

The actual mechanism of the improved properties obtained in the instant invention is not clearly understood. It is, however, believed that acidulation of silicate below a certain pH, preferably around neutral pH, results in a large number of nuclei. The post-treatment of silica slurry with silicate solution results in the growing of particles and making the particles more uniform. Because of the uniformity of the particles, the oil and the void volume increases. This also explains the increase in friability.

The growth of particles results in a decrease of surface area. This is attributed to the dissolution of small particles and then reprecipitation in the form of large particles. This then gives a silica product of predominantly more uniform size than the prior art silica. Because of the loss of some nuclei in the post-treatment process, the surface area decreases.

EXAMPLES III, IV AND V

The procedures of Example I were repeated except that the precipitated silica reaction slurry prior to filtration thereof was post-treated with silicate solution which corresponded to the treatment level of 30% (Example III), 50% (Example IV), and 70% (Example V). The volume of silicate solution required for post-treatment silica slurry in Examples III, IV, and V is as follows:

| Example No. | % Treatment | Post-Treatment Volume of Silicate Solution |
|---|---|---|
| III | 30 | 11.35 liters |
| IV | 50 | 18.92 liters |
| V | 70 | 26.50 liters |

Data obtained in Examples I through V is listed in Table II.

TABLE II

| Example No. | % Treatment Level | % WCM | Structure Index | Oil Absorption | Void Volume | BET Surface Area | Percent Friability |
|---|---|---|---|---|---|---|---|
| I | 0 | 86.0 | 615 | 172 | 2.95 | 164 | 10 |
| II | 10 | 83.5 | 505 | 190 | 3.55 | 141 | 20 |
| III | 30 | 82.0 | 455 | 202 | 4.14 | 123 | 98 |
| IV | 50 | 81.9 | 452 | 200 | 4.07 | 120 | 60 |
| V | 70 | 79.8 | 395 | 197 | 4.05 | 153 | 40 |

The following conclusions can be drawn by examining the data of Table II.

1. The treatment level, as it increases, results in the decrease of structure index.
2. The oil absorption increases with the increase in the treatment level, and the oil absorption appears to go through a maximum at 30% treatment level.
3. The particle-particle void volume also follows the same trend as the oil absorption data. The void volume increases with increase in the treatment level and appears to go through a maximum at about 30% treatment level.
4. The BET surface area decreases, appears to go through a minimum at 50% treatment level and then increases.
5. The percent friability follows the same trend as the oil absorption. The friability of silica increases with increase in the post-treatment level and goes through a maximum friability at 30% treatment level.

It is clear from the data listed in Table II that improvements which result from post-treatment of the precipitated silica reaction slurry are unique and were truly unexpected.

The improved properties obtained by the practice of the instant invention are depicted in FIGS. 1 through 5.

FIG. 1 is a graph illustrating the change in the structure index of silica as a function of silicate post-treatment.

Figure 2:
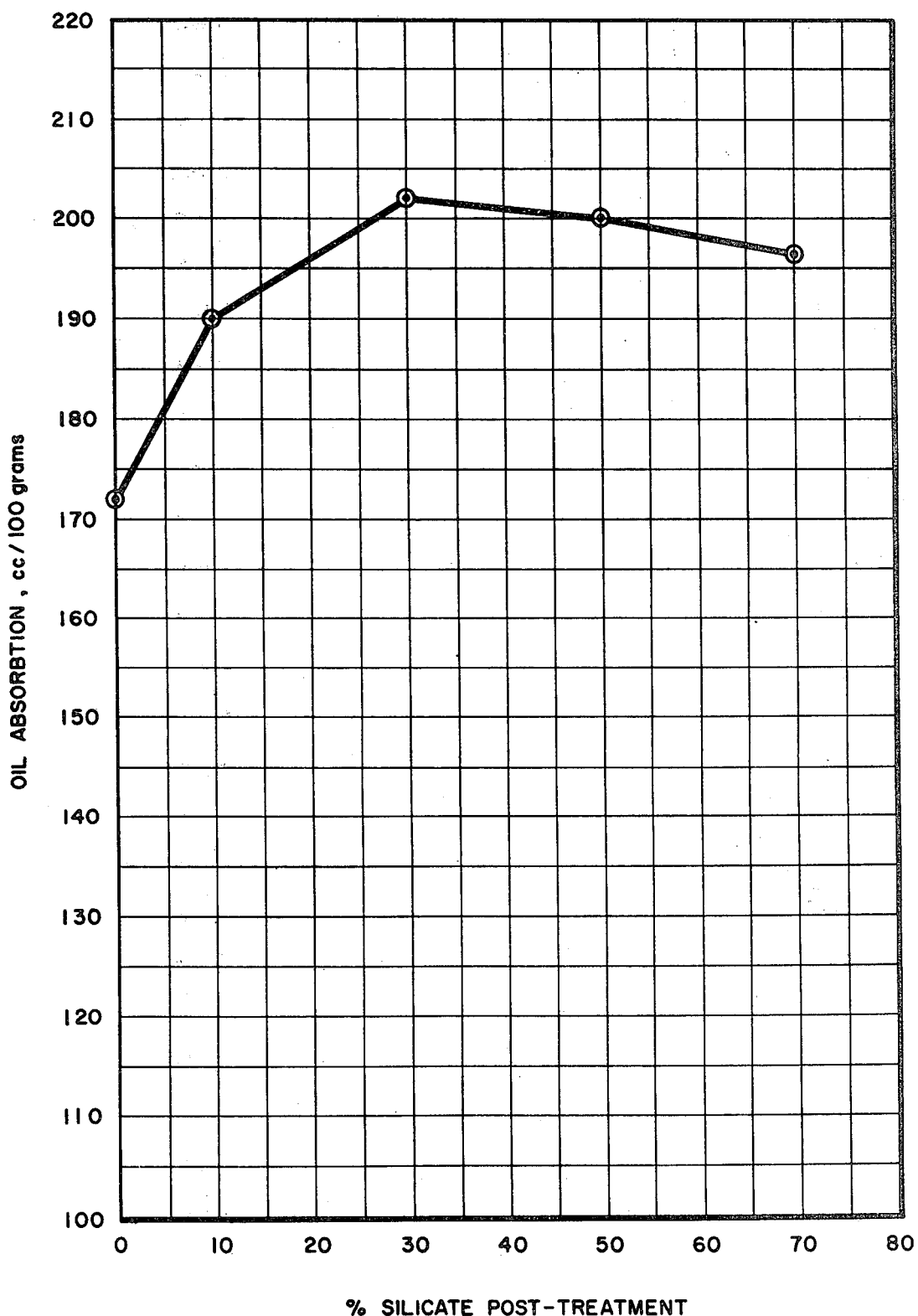
FIG. 2 is a graph illustrating the change in the oil absorption of silica as a function of silicate post-treatment.

FIG. 2 is a graph illustrating the change in the oil absorption of silica as a function of silicate post-treatment.

Figure 3:
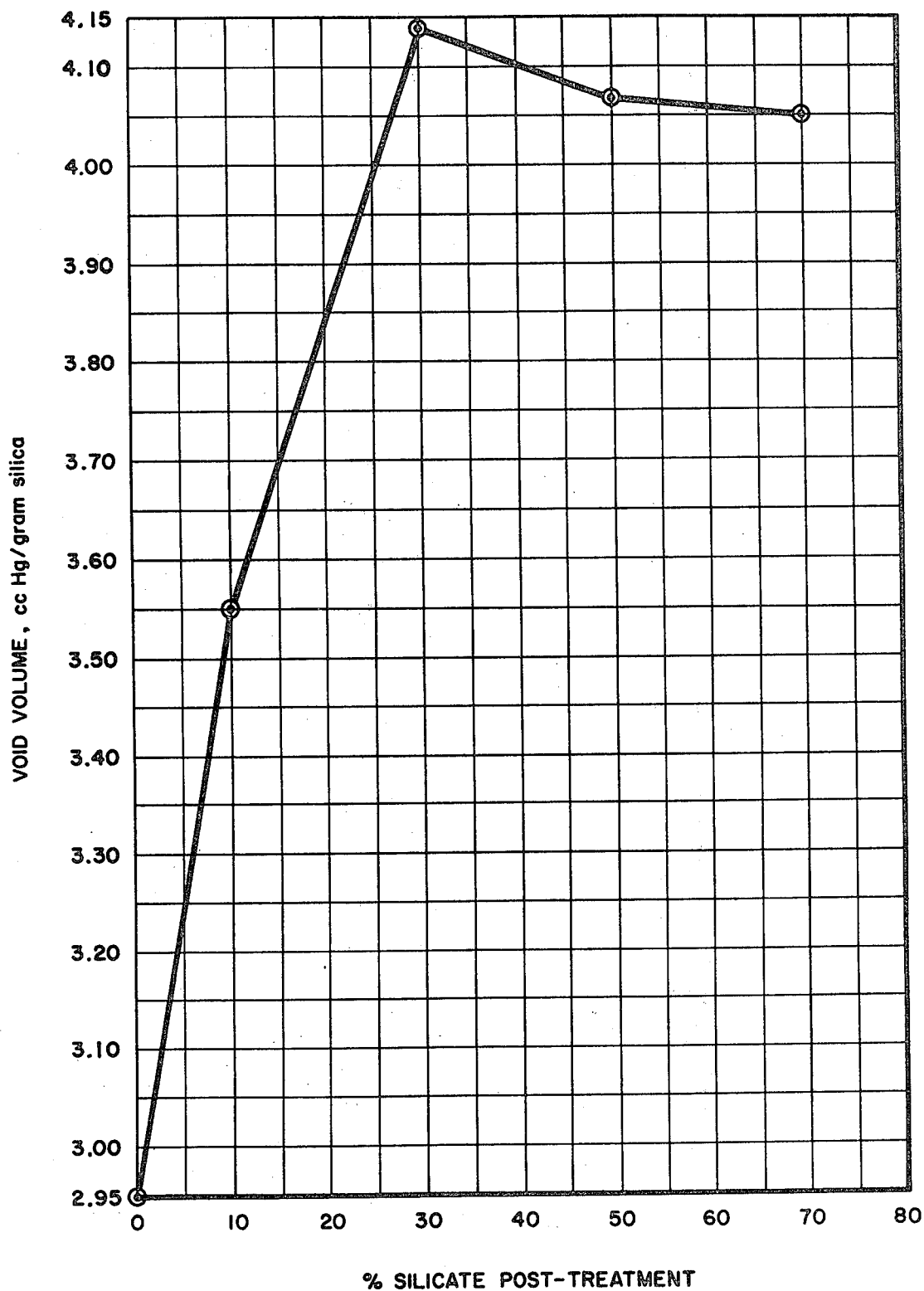
FIG. 3 is a graph illustrating the change in the void volume of silica and function of silicate post-treatment.

FIG. 3 is a graph illustrating the change in the void volume of silica as a function of silicate post-treatment.

Figure 4:
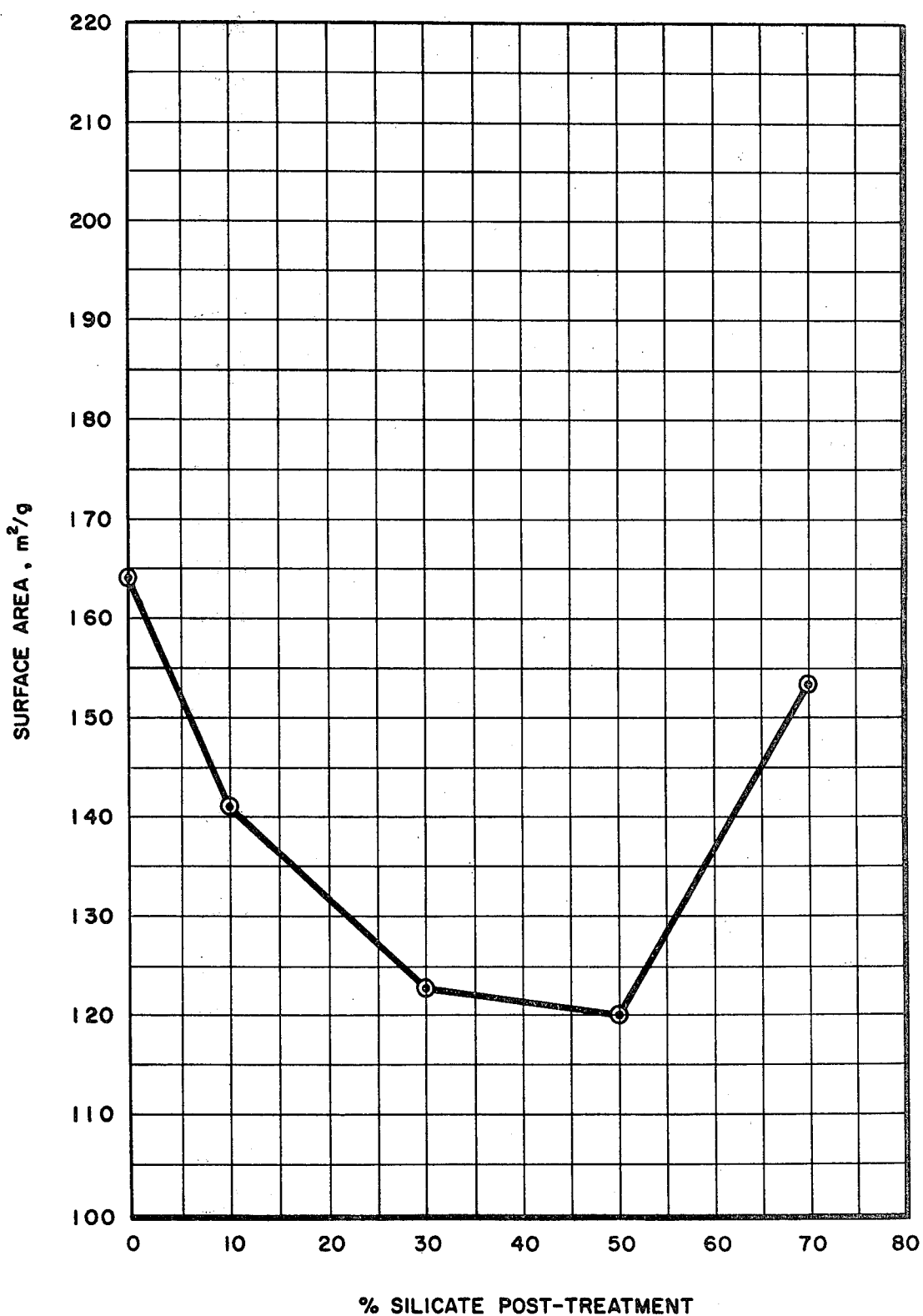
FIG. 4 is a graph illustrating the change in the surface area of silica as a function of silicate post-treatment.
Figure 5:
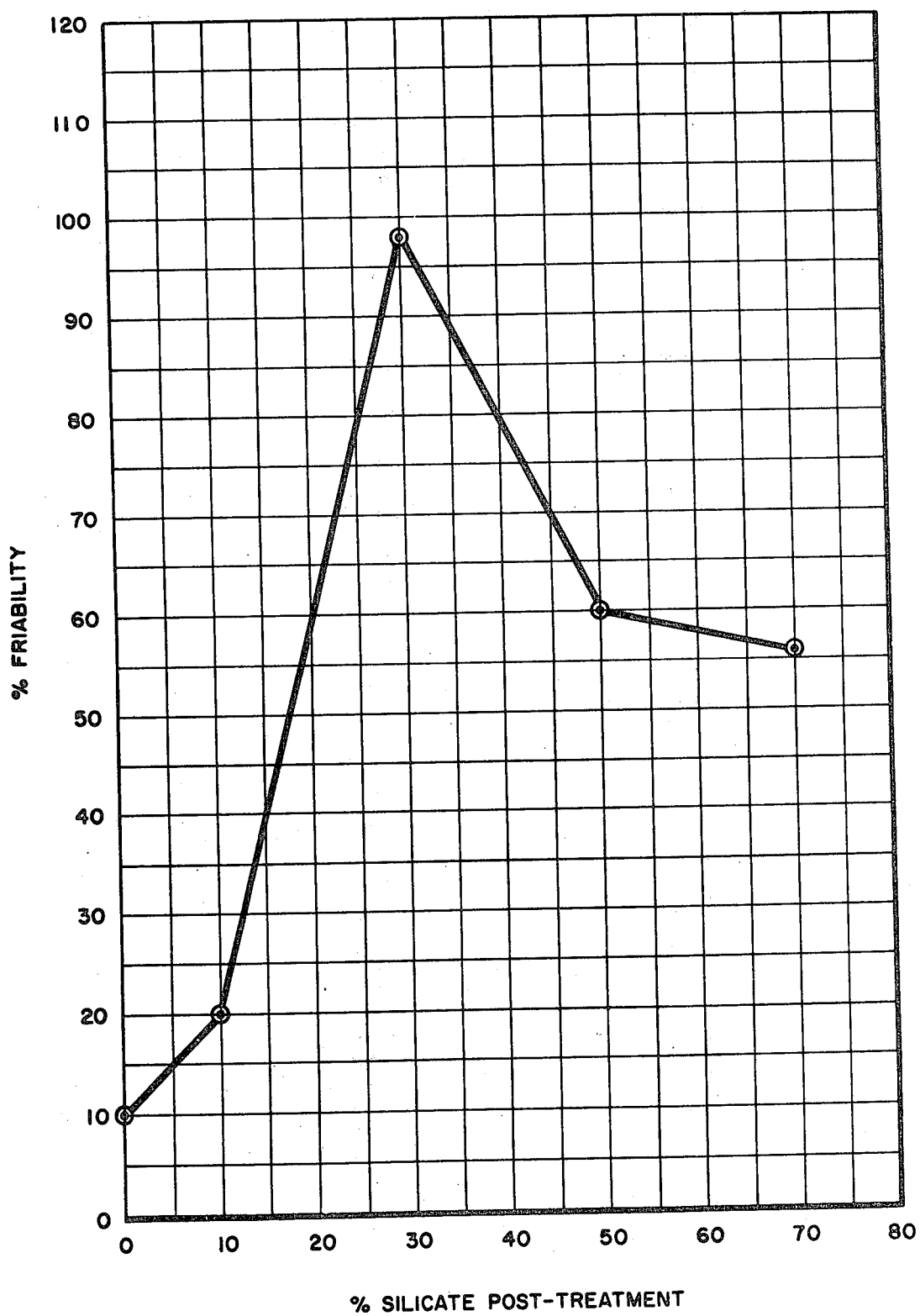
FIG. 5 is a graph illustrating the percent change in friability of silica as a function of silicate post-treatment.

FIG. 4 is a graph illustrating the change in the BET surface area of silica as a function of silicate post-treatment FIG. 5 is a graph illustrating the percent change in friability of silica as a function of silicate post-treatment.

In the practice of the invention it has been found that processing parameters can be varied in certain ranges as follows.

The process can be conducted at a reaction temperature between 60° C.–95° C. Ideal results were obtained when the reaction temperature of 80° C. was used. This process cannot be conducted below 60° C. Below 60° C. a white, transparent, gel-like product is obtained which does not possess suitable pigmentary properties.

The acid temperature can be varied between 32° C. to 65° C. Ideal results were obtained when the acid temperature was maintained at 38° C.

The silicate used for the post-treatment can be of the same or different concentration when compared with initial silicate used for acidulation to a final pH of 7. The silicate used for post-treatment may be added gradually as a function of time or it can be metered into the reaction slurry as fast as possible.

The temperature of the silicate solution used for post-treating the precipitated silica reaction slurry can be varied between 32° C.–75° C. Experiments led to the conclusion that an ideal temperature of silicate prior to treating the precipitated silica slurry should be 65° C.

While the prior art silica cannot be used for dentifrice application, it was discovered that silicas produced by the instant improved process were suitable for dentifrice use. For use in clear-gel dentifrices, the refractive index of the silica was controlled by up-grading to a value between 1.45 to 1.46 by pre-mixing acid with an adduct material. The suitable adduct material is a solution of alum or aluminum sulfate, soluble calcium magnesium, and zinc compounds.

A series of experiments was run in which the adduct material was pre-mixed with the acid. For these tests, a stock solution of acid and adduct material was prepared by mixing 100 liters of 11.4% acid with 7 liters of 15% aluminum sulfate solution. This mixed acid-alum solution was used for acidulation of silicate. The following experiment were run similar to Example I through V except that acid contained a small quantity of alum as specified above to produce controlled refractive index silicas.

EXAMPLES VI, VII, VIII, IX, & X
Post-Treatment

| Example No. | % Treatment | Volume Silicate Solution Required |
|---|---|---|
| VI | 0 | 0 liters |
| VII | 10 | 3.78 liters |
| VIII | 30 | 11.35 liters |
| IX | 50 | 18.92 liters |
| X | 70 | 26.50 liters |

Data obtained in Examples VI through X is listed in Table III. Table IIIA shows the effect of the adduct addition and post-treatment on the surface area and refractive index values of silicas.

TABLE III

PROPERTIES OF CONTROLLED REFRACTIVE INDEX SILICAS AS A FUNCTION OF POST-TREATMENT LEVEL

| Example No. | % Treatment Level | % WCM | Structure Index | Oil Absorption | Void Volume | BET Surface Area | Percent Friability |
|---|---|---|---|---|---|---|---|
| VI | 0 | 85.6 | 595 | 185 | 3.03 | 239 | 0 |
| VII | 10 | 83.2 | 495 | 201 | 4.00 | 220 | 28 |
| VIII | 30 | 81.3 | 435 | 212 | 4.44 | 153 | 93 |
| IX | 50 | 78.7 | 370 | 205 | 3.67 | 185 | 78 |
| X | 70 | 77.9 | 350 | 193 | 3.19 | 198 | 45 |

TABLE IIIA

EFFECT OF ADDUCT AND POST-TREATMENT ON PROPERTIES OF SILICA

| % Treatment | Silica W/Adduct | | Silica W/O Adduct | | Increase in Surface Area Due to Adduct and Treatment |
|---|---|---|---|---|---|
| | Surface Area (Table III) | Refractive Index | Surface Area (Table II) | Refractive Index | |
| 0 | 239 | 1.455 | 164 | 1.440 | 75 |
| 10 | 220 | 1.456 | 141 | 1.442 | 79 |
| 30 | 153 | 1.460 | 123 | 1.442 | 30 |
| 50 | 185 | 1.461 | 120 | 1.441 | 65 |
| 70 | 198 | 1.455 | 153 | 1.441 | 45 |

The following conclusions can be drawn by examining data listed in Table III.

1. The increase in the treatment level decreases the structure index of controlled refractive index silicas of Examples VI through X.

2. The oil absorption values of controlled refractive index silicas increase with the increase in the treatment level. The maximum oil absorption was obtained at about 30% treatment level.

3. The particle-particle void volume of controlled refractive index silicas increased as a function of the treatment level. A maximum increase was observed at a treating level of 30%.

4. The surface area decreased as a function of the treating level. Of all the silicas in Examples VI through X, a minimum surface area was observed at 30% treatment level. Note that in general the surface area of silicas in Examples VI through X is higher than the corresponding counterparts in Example I through V.

This increase in surface area is due to the presence of a small amount of an adduct material which was pre-mixed with the acid prior to producing controlled refractive index silicas of Examples VI through X. It is critical that the adduct material is pre-mixed with acid. If this is not done, the controlled refractive index silicas cannot be prepared.

5. The percent friability of the controlled refractive index silica increases as the post-treatment level increases. A maximum friability was observed at a level of 30% post-treatment.

The improved properties obtained (see Examples VI through X) in the practice of the instant invention are depicted in FIGS. 6 through 10.

Figure 6:
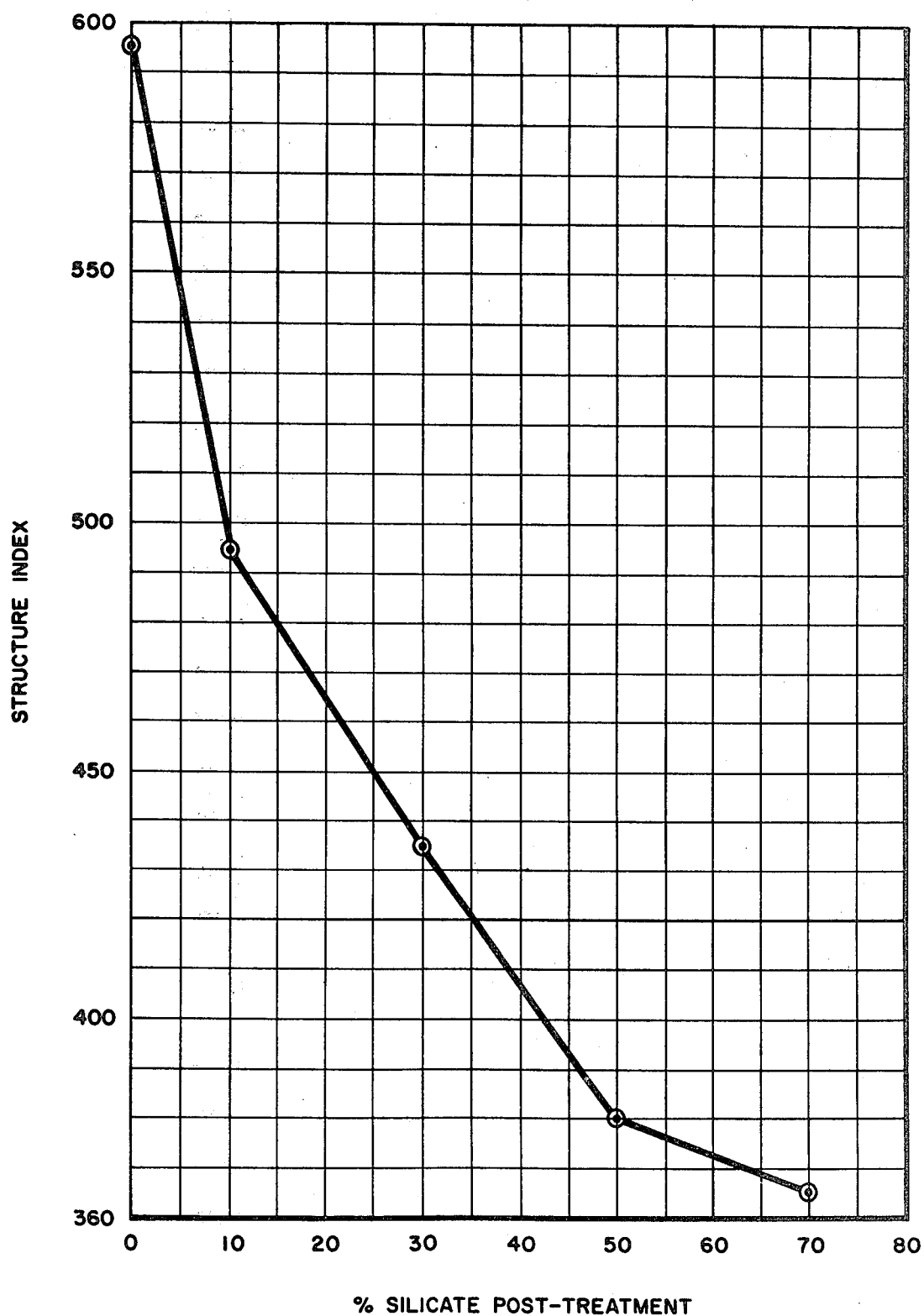
FIG. 6 is a graph illustrating how the structure index of the controlled refractive index silicas changes as a function of the silicate post-treatment.

FIG. 6 is a graph illustrating how the structure index of the controlled refractive index silicas changes as a function of the silicate post-treatment.

Figure 7:
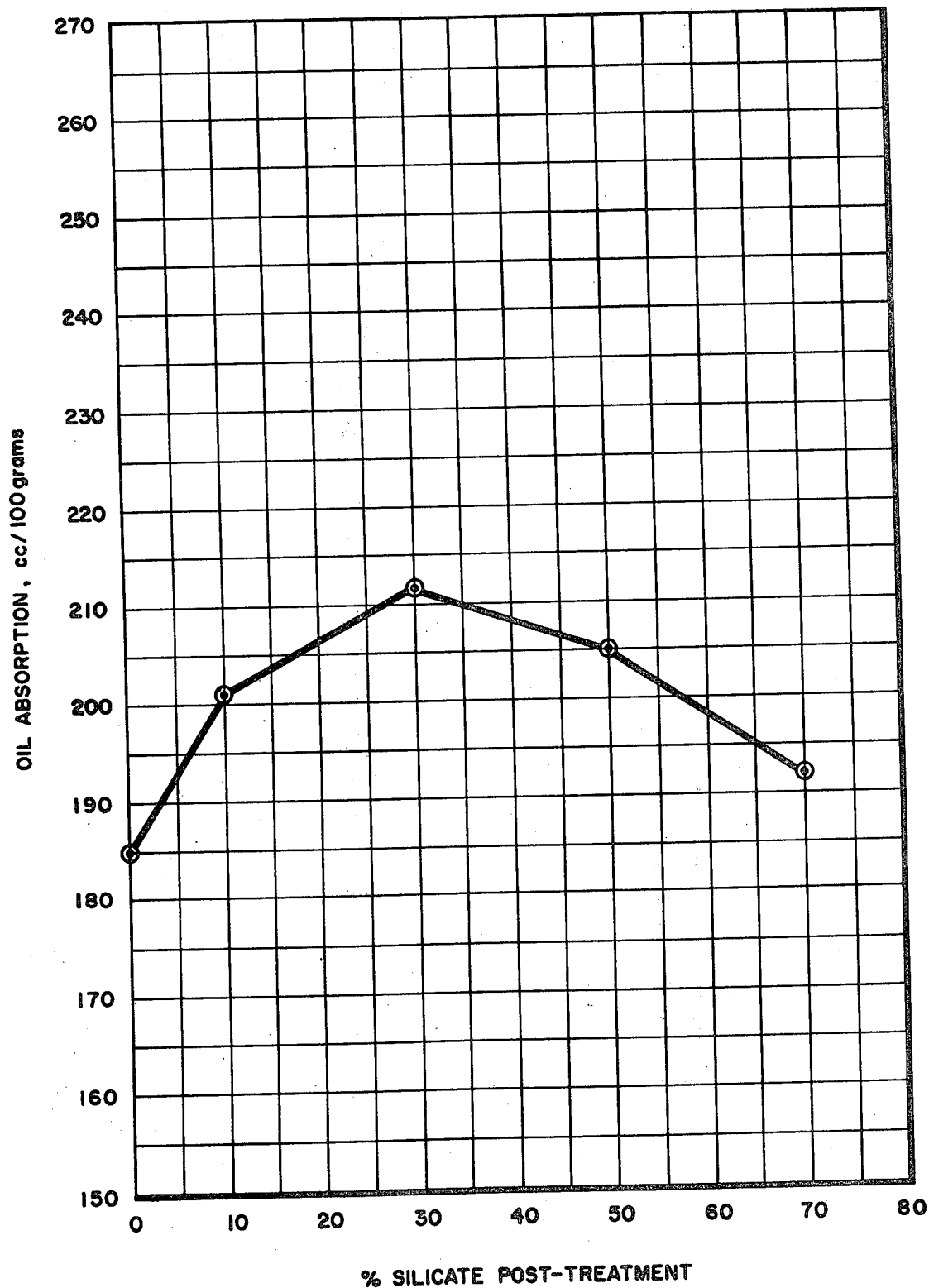
FIG. 7 is a graph illustrating how the oil absorption of the controlled refractive index silicas changes as a function of the silicate post-treatment.

FIG. 7 is a graph illustrating how the oil absorption of the controlled refractive index silicas changes as a function of the silicate post-treatment.

Figure 8:
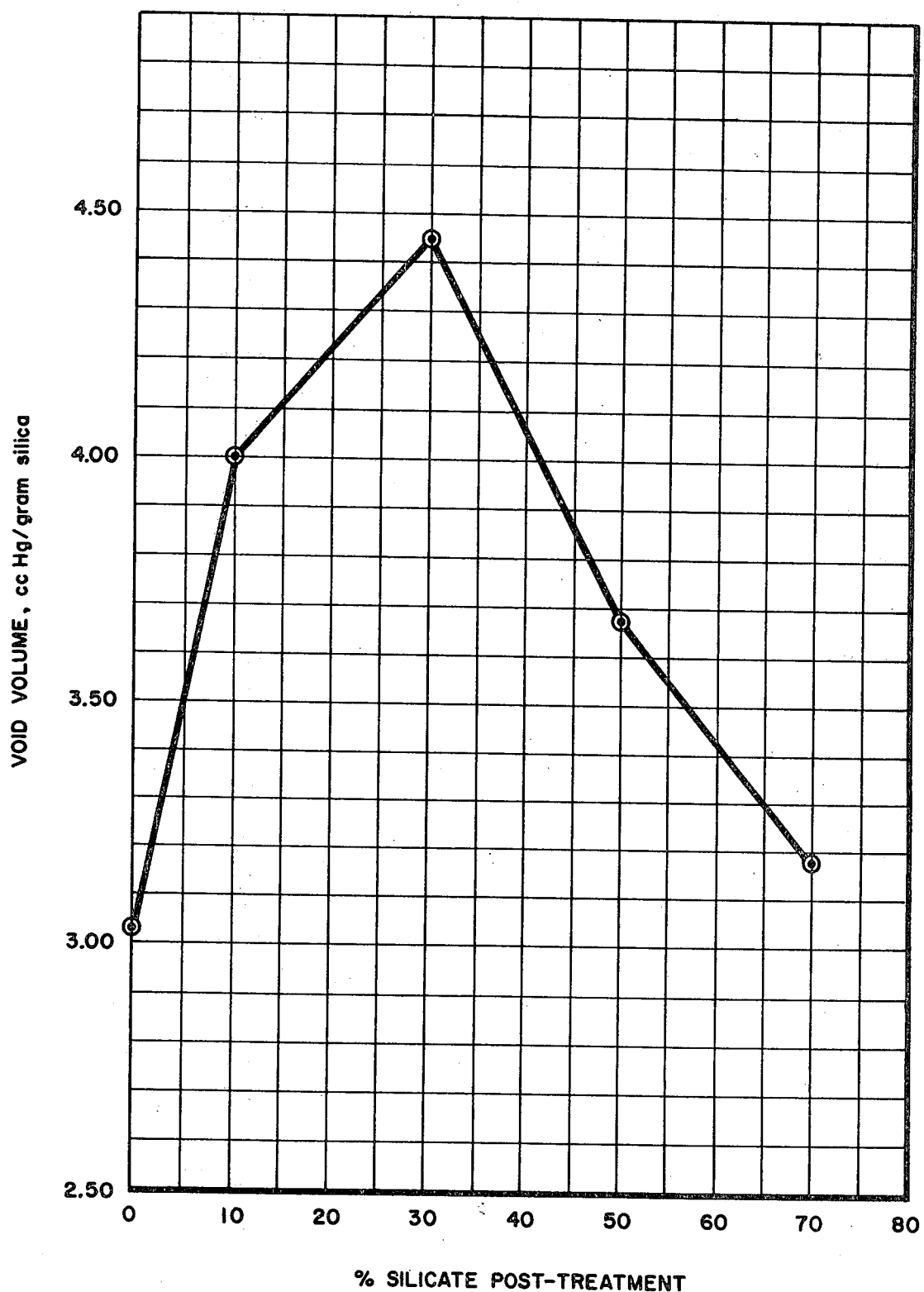
FIG. 8 is a graph illustrating how the void volume of the controlled refractive index silicas changes as a function of the silicate post-treatment.

FIG. 8 is a graph illustrating how the void volume of the controlled refractive index silicas changes as a function of the silicate post-treatment.

Figure 9:
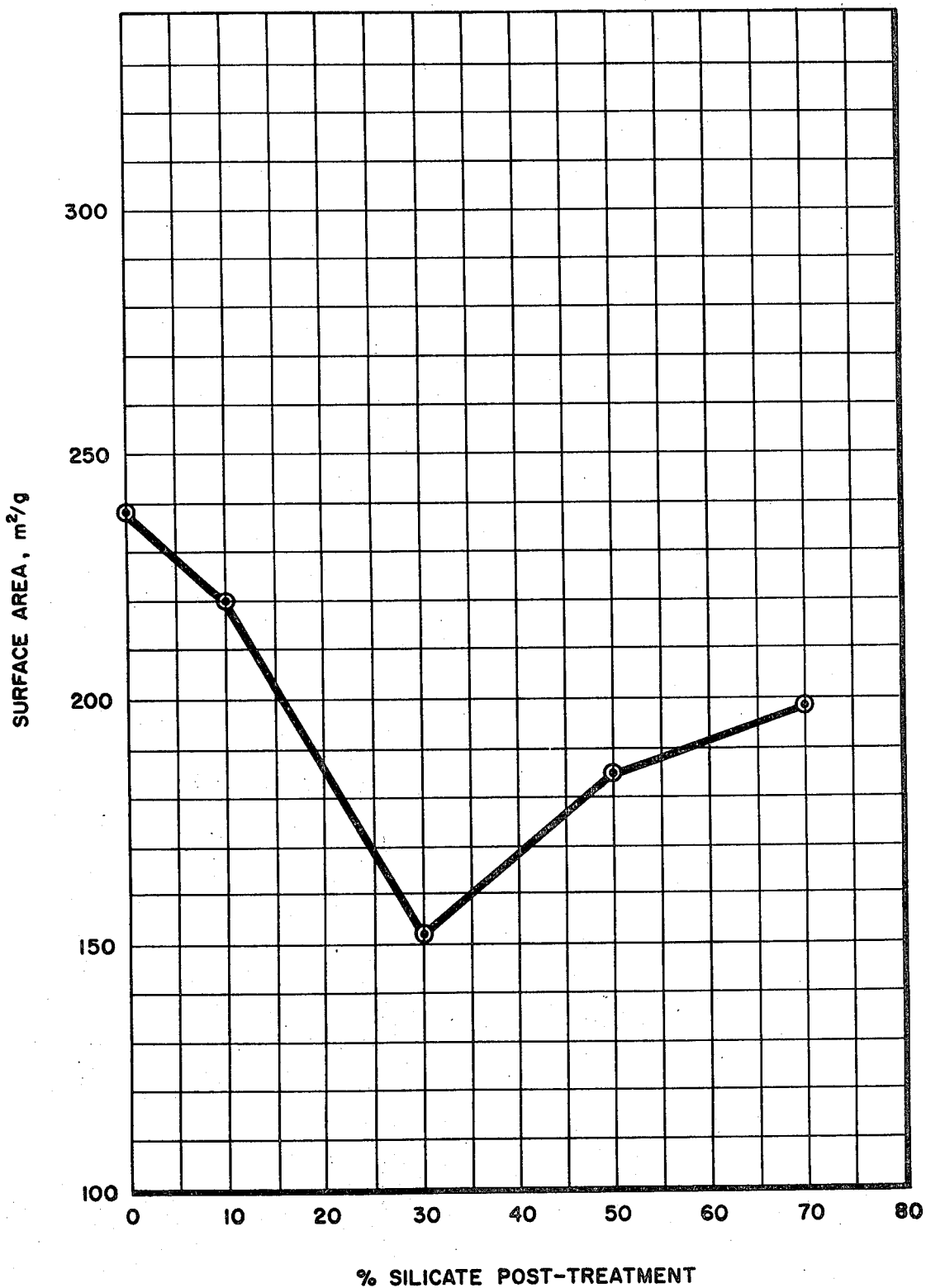
FIG. 9 is a graph illustrating how the surface area of the controlled refractive index silicas changes as a function of the silicate post-treatment.

FIG. 9 is a graph illustrating how the BET surface area of the controlled refractive index silicas changes as a function of the silicate post-treatment.

Figure 10:
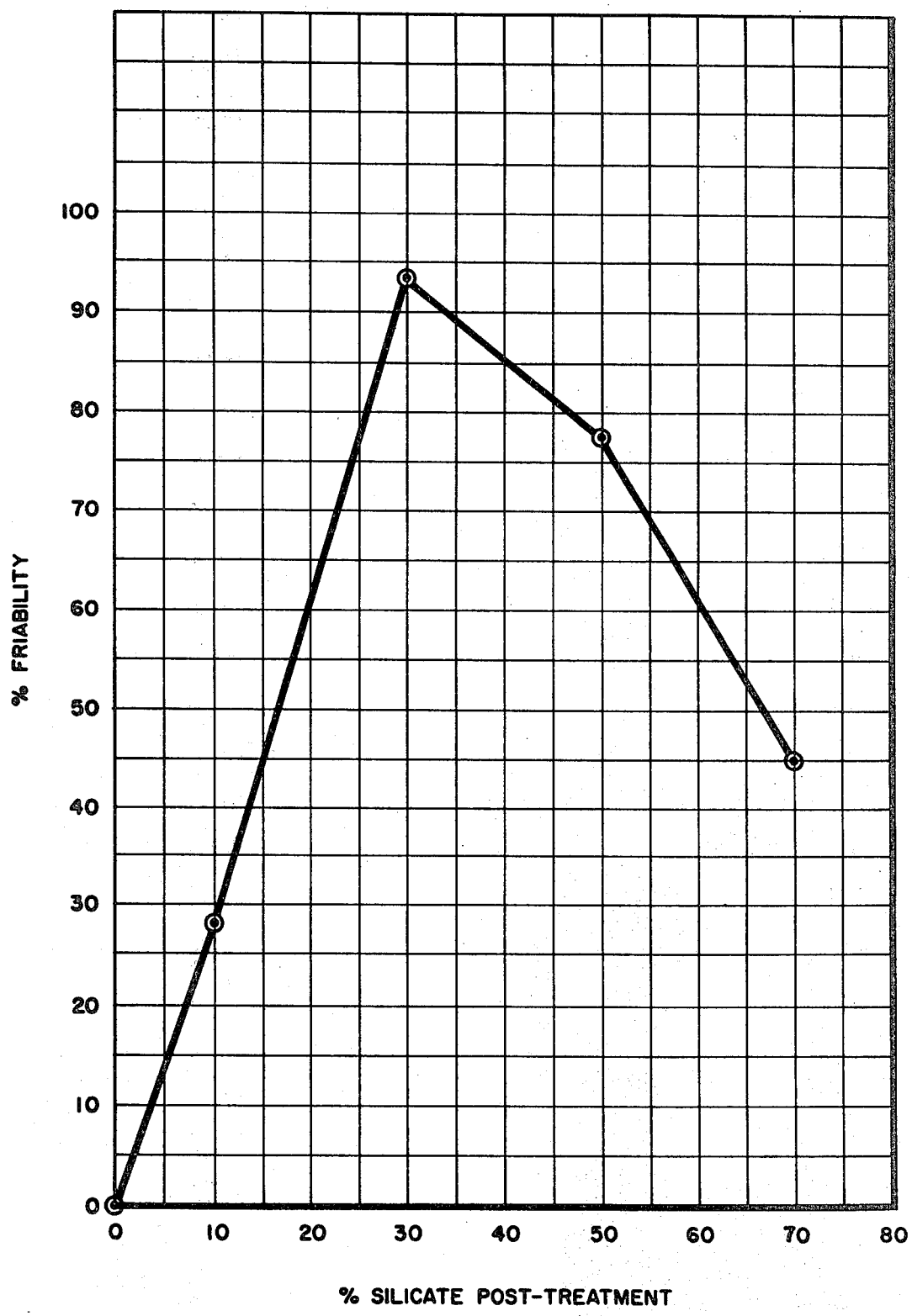
FIG. 10 is a graph illustrating how the percent friability of the controlled refractive index silica changes as a function of the silicate post-treatment.

FIG. 10 is a graph illustrating how the percent friability of the controlled refractive index silica changes as a function of the silicate post-treatment.

EFFECT OF SILICATE COMPOSITION, EXAMPLES XI–XXII

To further study the improvements of the instant invention, silicates of different compositions and concentration were used. The reaction slurry after post-treatment was treated with silicate solutions which corresponded to 20% conditioned level. Three different silicate solutions designated "A", "B", and "C" were used for this study.

Silicate Solution "A" had a composition of 3.77% $Na_2O$, 12.23% $SiO_2$, and specific gravity of 1.139.

Silicate Solution "B" had a composition of 3.30% $Na_2O$, 10.7% $SiO_2$, and a specific gravity of 1.120.

Silicate Solution "C" had a composition of 2.82% $Na_2O$, 9.18% $SiO_2$, and a specific gravity of 1.101.

In each case a control silica (without treatment) was prepared similar to teachings of Example I. Post-treated silicas were prepared following the procedures of Example II. Data is summarized in Table IV.

TABLE IV

SILICAS FROM DIFFERENT SILICATE SOLUTIONS

| Example No. | % Treatment | Silicate Solution | % WCM | SI | BET Surface Area, $m^2/g$ | Oil Absorption (cc/100 g) | Void Volume (cc Hg/g) |
|---|---|---|---|---|---|---|---|
| XI* | 0 | A | 84.4 | 540 | 200 | 195 | 3.33 |
| XII | 20 | A | 82.8 | 482 | 186 | 208 | 4.01 |
| XIII* | 0 | B | 85.1 | 570 | 208 | 206 | 3.09 |
| XIV | 20 | B | 83.6 | 510 | 200 | 221 | 3.92 |
| XV* | 0 | C | 86.8 | 656 | 247 | 175 | 2.57 |
| XVI | 20 | C | 85.0 | 567 | 226 | 187 | 2.71 |

*Control experiments (without treatment).

The data of Table IV again substantiates that the post-treatment of the silica reaction slurry as per the instant invention results in a decrease in the structure index and the surface area but an increase in the oil absorption and the particle-particle void volume of silicas. This was truly unexpected.

In a further series of experiments, Examples XI through XVI were repeated except that a calculated amount of an aluminum sulfate solution (as disclosed in Examples VI through X) was pre-mixed with the acid. The aluminum sulfate solution was added to the acid in order to produce silica products having a controlled refractive index for use in dentifrice compositions. Data obtained in the preparation of controlled refractive index silicas is listed in Table V.

TABLE V

CONTROLLED REFRACTIVE INDEX SILICAS*

| Example No. | % Treatment | Silicate Solution | % WCM | SI | BET Surface Area, $m^2/g$ | Oil Absorption (cc/100 g) | Void Volume (cc Hg/g) |
|---|---|---|---|---|---|---|---|
| XVII** | 0 | A | 84.6 | 550 | 224 | 194 | 3.31 |
| XVIII | 20 | A | 82.2 | 462 | 174 | 219 | 3.98 |
| XIX** | 0 | B | 85.5 | 590 | 249 | 188 | 2.84 |
| XX | 20 | B | 82.8 | 482 | 210 | 221 | 3.44 |
| XXI** | 0 | C | 86.4 | 645 | 322 | 177 | 2.57 |
| XXII | 20 | C | 84.3 | 536 | 243 | 187 | 3.01 |

*Refractive index of all silicas in Table V was 1.45–1.46.
**Control experiments (without treatment)

By examination of the data in Table V, it will be seen that the surface area of controlled refractive index silicas is higher than their corresponding counterparts listed in Table IV. This is thought to be due to microporosity which is created in the silica particles by the addition of adduct material. It is clear from the data of Table V that controlled refractive index silicas wherein the precipitated silica reaction slurry is post-treated results in a decrease in structure index and decrease in surface area, but an increase in oil absorption and particle-particle void volume. This result, wherein the reduction in the structure index without a corresponding reduction in the oil absorption, is truly unexpected. It is taught in the prior art that as the wet cake moisture decreases, the oil absorption of a silica also decreases. By the practice of the instant invention, it is now possible to increase the oil absorption of a pigment without increasing the wet cake moisture or structure index of silica. Stated differently, the instant invention results in a fantastically unique technique wherein it is now possible to increase the oil absorption of a silicon dioxide without increasing the wet cake moisture or production cost of a pigment. In fact, the process of the invention results in a silica pigment of higher oil absorption and yet lower production costs.

Silica Containing Compositions

As noted above, the silicon dioxides of the instant invention can be used for various applications. As shown by FIGS. 1 through 10, silica products produced by the practice of the instant invention have particularly and especially desirable physical and surface chemical properties. For use as a pigment in rubber, paper, paints, detergents, dentifrice, and conditioning applications, it is desirable that the silica have a controlled particle size, surface area, oil absorption, refractive index, particle-particle void volume, and structure index. As a consequence of the remarkable physical, chemical properties of the silica pigments of the present invention, they are superior for use in rubber, paper, paint, detergent, dentifrice, and conditioning use as compared with prior art silica products.

Rubber Compositions

The following materials, in the quantities and the manner indicated, describe a standard testing composition employed to test the products of the invention in rubber for use in shoe soles, heels, and the like:

| Test recipe - rubber in shoe soles and heels: | Parts by wt./100 |
|---|---|
| (1) Styrene-butadiene rubber (Plioflex 1778-SBR, nondiscoloring low temperature polymer containing 37 parts light color naphthenic oil per 100 parts cold rubber-Mooney viscosity 42–45) | 42.8 |
| (2) Styrene-butadiene rubber (Plioflex 1510-white, solid low temperature cold rubber-Mooney viscosity of 29–36) | 35.0 |
| (3) Styrene-butadiene rubber (Plioflex 1950-white, friable mixture of 50% low temperature SBR containing 37 parts of naphthenic oil and 50% high styrene resins) | 93.6 |
| (4) Zinc oxide | 6.6 |
| (5) Zeolex ® 23 (synthetic pigment material | |

TABLE VI

|  | Rubber Data, Silica of Examples I through V | | | | | |
|---|---|---|---|---|---|---|
|  | Ex. I | Ex. II | Ex. III | Ex. IV | Ex. V | Hi-Sil 233 |
| 95% Cure, min | 4.25 | 4.58 | 4.08 | 4.16 | 4.33 | 4.92 |
| Scorch time, min | 1.33 | 1.67 | 1.42 | 1.42 | 1.42 | 1.80 |
| Tensile strength, p.s.i.* | 2200 | 2075 | 1875 | 1900 | 1908 | 2142 |
| Modulus, 300% p.s.i.* | 875 | 926 | 1042 | 983 | 941 | 825 |
| Modulus, 400% p.s.i.* | 1175 | 1250 | 1325 | 1292 | 1242 | 1100 |
| Elongation, percent* | 608 | 573 | 533 | 542 | 550 | 625 |
| Shore A Hardness* | 85 | 88 | 86 | 86 | 88 | 86 |
| NBS Abrasion* | 62 | 75 | 70 | 70 | 65 | 63 |

*8 minute cure

| Test recipe - rubber in shoe soles and heels: | Parts by wt./100 |
|---|---|
| produced according to U.S. Pat. No. 2,739,073) | 7.0 |
| (6) Pigment (products of Examples I through V herein) | 70.0 |
| (7) Stearic acid | 1.0 |
| (8) Carbowax-(polyglycol-6000 molecular weight) | 4.0 |
| (9) Phthalic anhydride | .65 |
| (10) NOBS Special (N-oxydiethylene benzothiazole-2-sulfenamide) | 1.00 |
| (11) Captax (mercaptobenzothiazole) | .80 |
| (12) DOTG (diorthotolylguanidine) | .80 |
| (13) Octamine (diphenylamine and diisobutylamine) | 1.0 |
| (14) Circo light oil (naphthenic type oil) | 15.0 |
| (15) Sulfur | 2.8 |

The following materials, in the quantities indicated, describe a standard testing composition employed to test the exemplary products herein in rubber for use in tires, more particularly, heavy-duty tires of the off-the-road type:

| Test recipe - off-road-tires: | Parts by wt. |
|---|---|
| (1) Rubber - (Natural smoked sheets) | 100.0 |
| (2) Carbon black (ISAF-intermediate super abrasion furnance black- J. M. Huber Corporation, Borger, Texas | 37.0 |
| (3) Pigment (end product of examples herein) | 20.0 |
| (4) Zinc oxide | 5.0 |
| (5) Stearic acid | 3.0 |
| (6) 6-dodecyl-1,2-dihydro-2,2,4-trimethyl quinoline (Santoflex DD) | 0.5 |
| (7) Polymerized 1,2-dihydro-2,2,4-trimethyl quinoline (Flectol H) | 1.5 |
| (8) Pine tar | 5.0 |
| (9) Terpene resin acid blend (Turgum S) | 2.0 |
| (10) 2,2'-Benzothiozyl disulfide (MBTS) | 0.8 |
| (11) Sulfur | 2.8 |
|  | 177.6 |

The silica pigments of Examples I through V and a commercial pigment Hi-Sil 233 (a product of PPG Industries, Inc.) were incorporated into the above-mentioned shoe heels and soles formulation and subjected to various conventional tests.

The physical tests and results are reported in Table VI.

From Table VI, it can be seen that the rubber compositions incorporating silica pigment prepared by the improved process of the instant invention have much higher modulus and abrasion resistance values than control silica of Example I and the reference standard Hi-Sil 233. These desirable properties of the instant invention make the rubber compositions useful for shoe heels and soles, tire treads and carcasses, engine mounts and belts.

Figure 11:
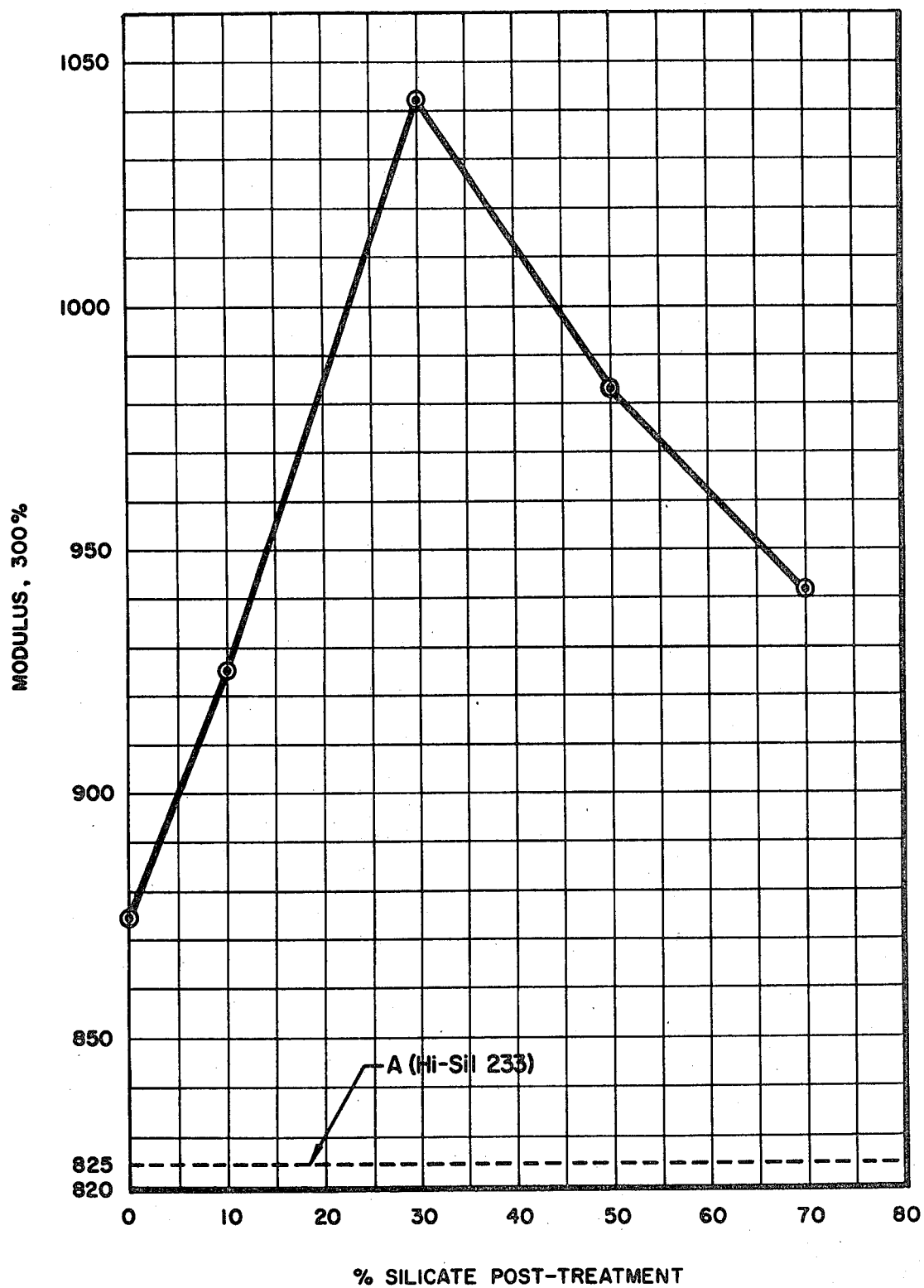
FIG. 11 is a graph illustrating the change in modulus values of rubber compositions comprising silica pigments of Examples I through V as a function of the percent silicate post-treatment.
Figure 12:
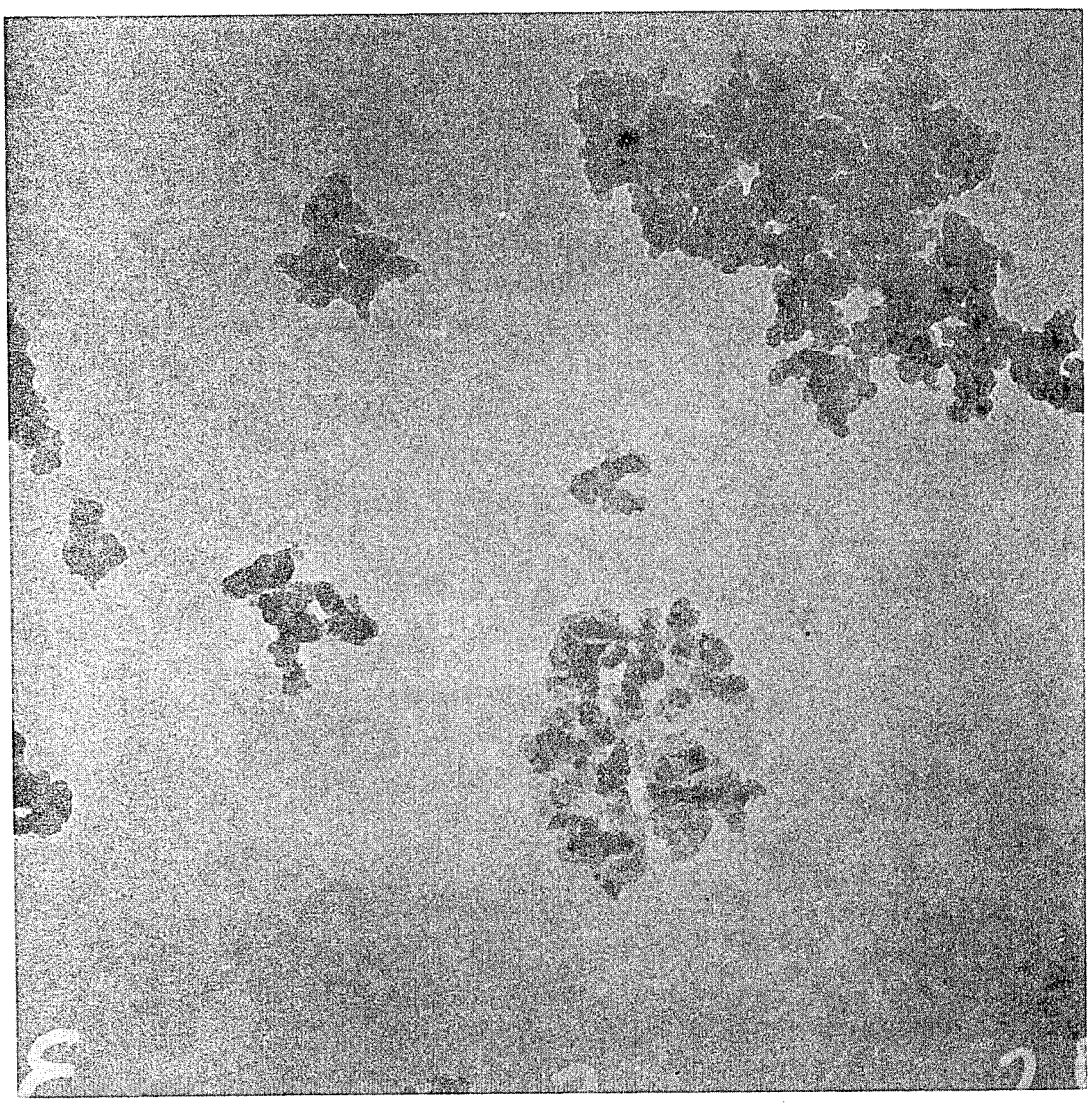
FIG. 12 is a microphotograph of the product of the invention with 10% post-conditioning, no adduct.
Figure 13:
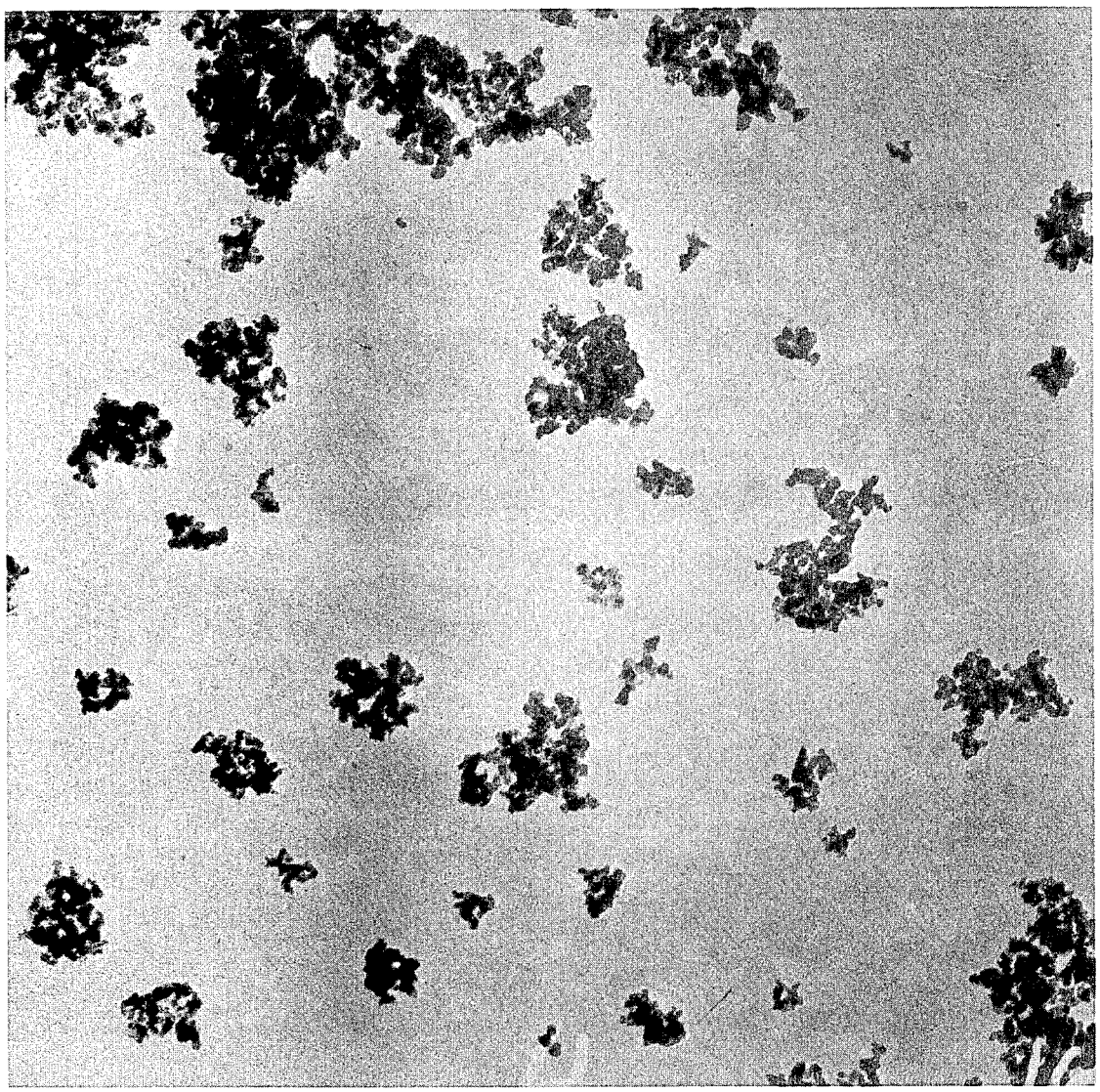
FIG. 13 is a microphotograph of the product of the invention with 30% post-conditioning, no adduct.
Figure 14:
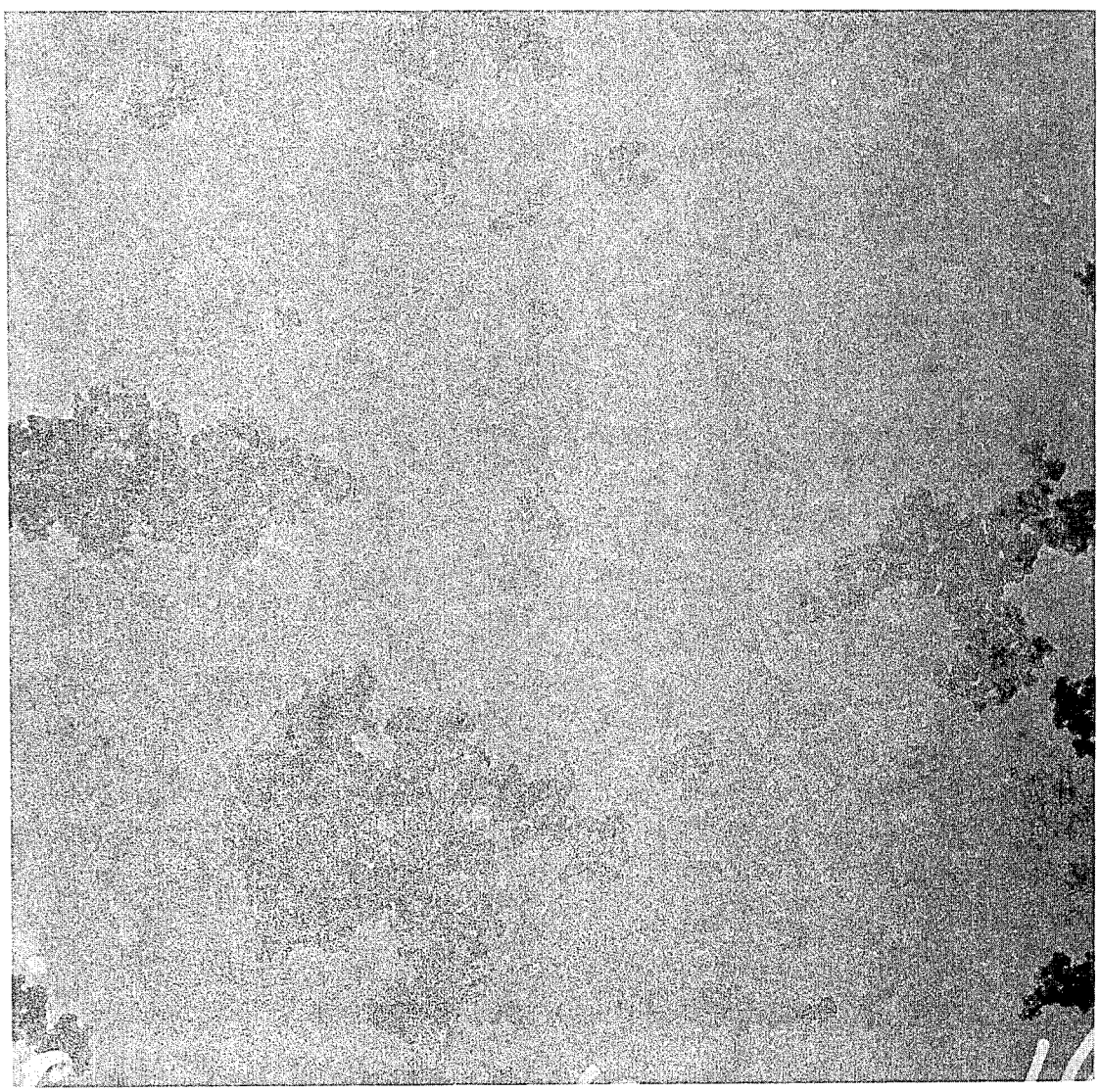
FIG. 14 is a microphotograph of the product of the invention with 70% post-conditioning, no adduct.
Figure 15:
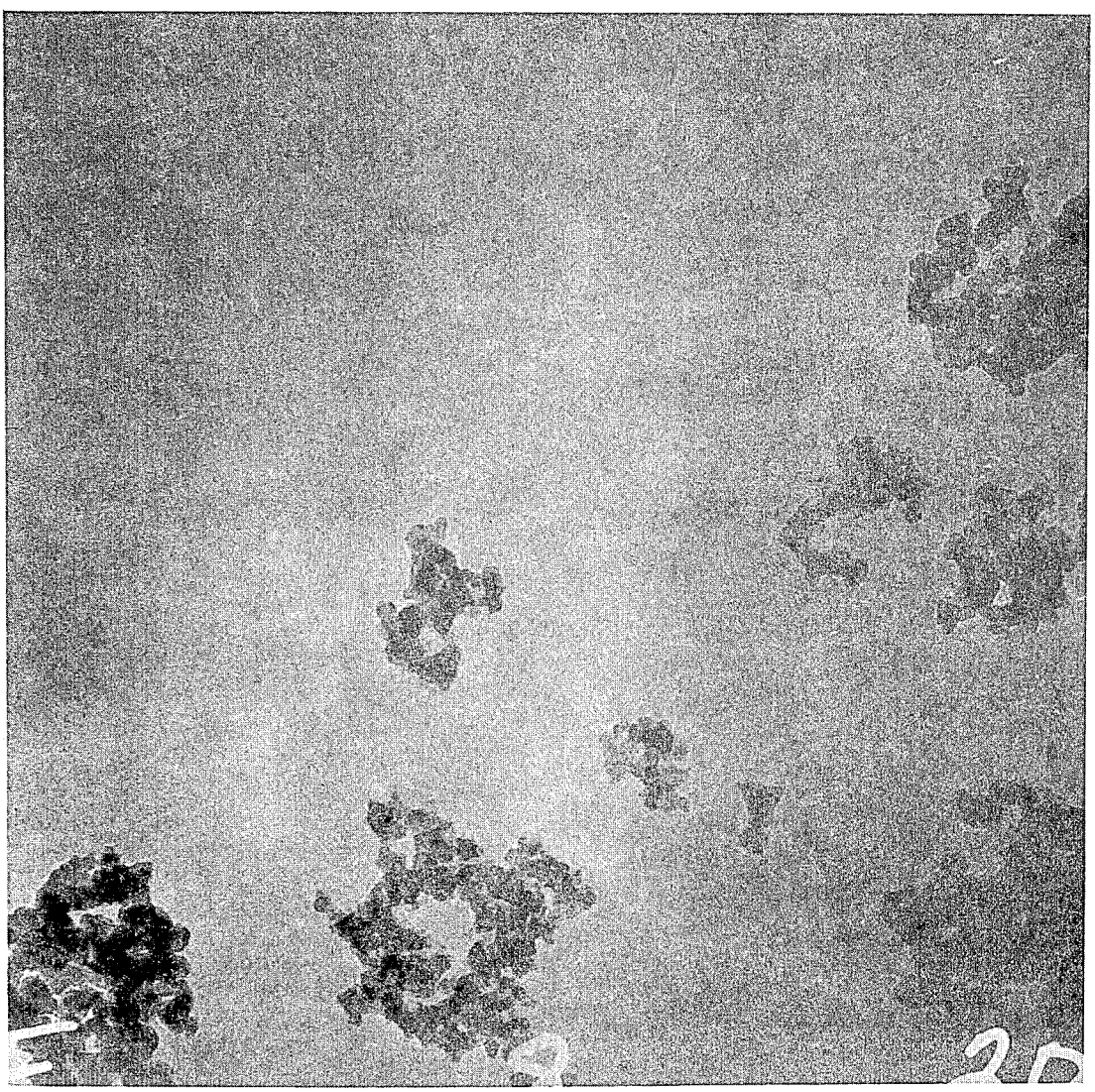
FIG. 15 is a microphotograph of the product of the invention with 20% post-treatment, with adduct, aluminum sulfate.
Figure 16:
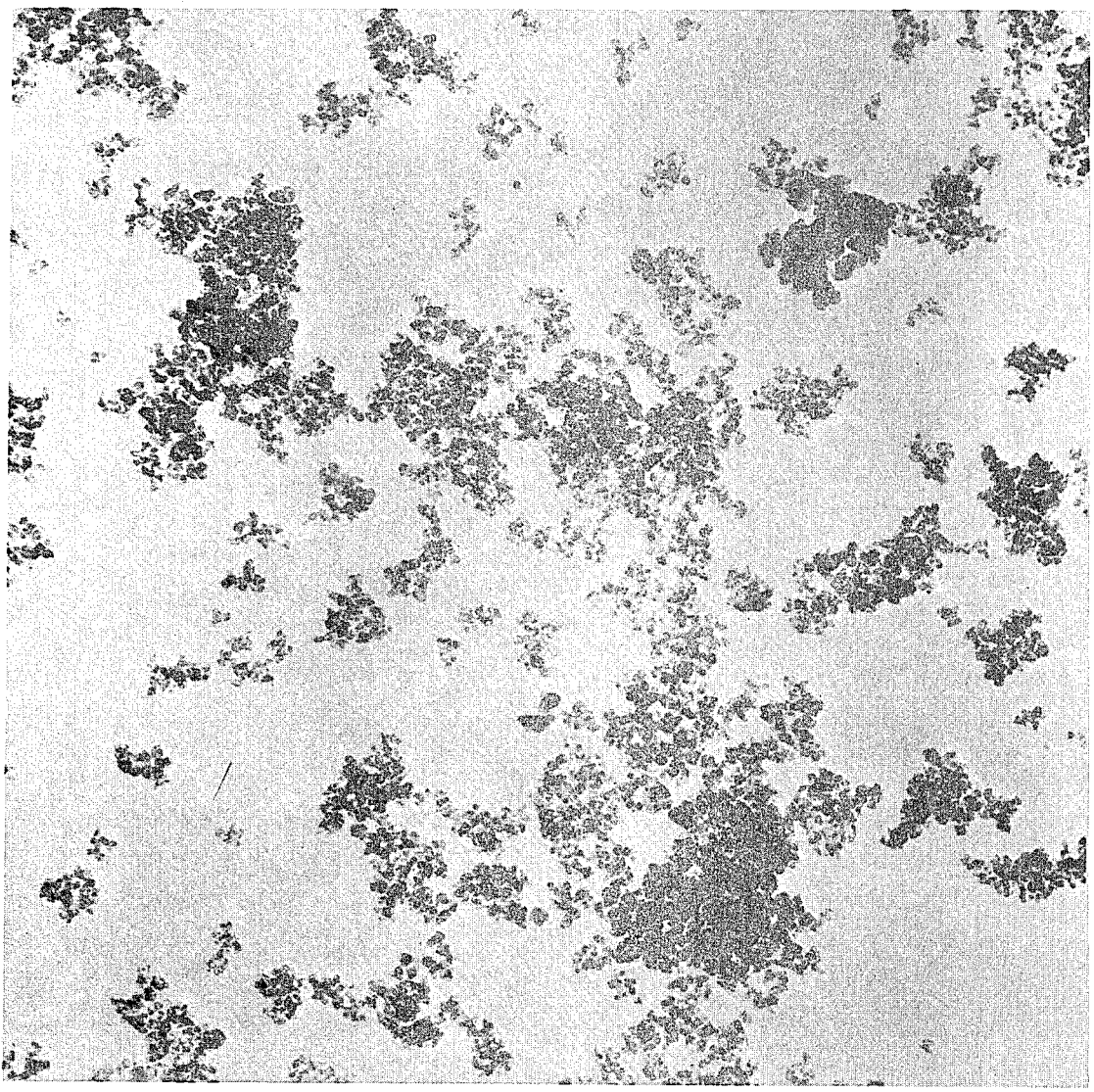
FIG. 16 is a graph illustrating a product of the prior art, no post-conditioning, acidulation of sodium silicate with sulfuric acid.

FIG. 11 illustrates the change in modulus values of rubber compositions comprising silica pigments of Examples I through V as a function of the percent silicate post-treatment. Thus, examining Table VI, it is clear that silica pigments of instant invention exhibit superior rubber reinforcing properties. See FIG. 11, line A for Hi-Sil 233-prior art product.

The rubbers (alternatively referred to herein as elastomers which materials are unvulcanized) which can be employed in the invention include both natural and synthetic rubbers. Exemplary of suitable synthetic rubbers are styrene-butadiene, butyl rubber, nitrile rubber, polybutadiene, polyisoprene, ethylene propylene, acrylic, fluorocarbon rubbers, polysulfide rubbers, and silicone rubbers. Mixtures or copolymers of the above synthetic rubbers can be employed alone or in combination with natural rubber. The preferred rubbers are nitrile rubber, styrene-butadiene rubber, natural rubber, polyisoprene, and mixtures because they are most compatible with polyester fibers although minor amounts of other rubbers can be included without adverse effects.

Paper Compositions Containing Silicas

The ease with which material printed on one side of a sheet can be seen through on the other is a print quality item that has been the subject of complaints, generally in the field of newspaper printing. This effect is frequently called "print show-through" or "print-through." It is always important to improve the printability of newsprint because printability is becoming increasingly more important to newspapers, their readers, and advertisers.

Silicas of Examples I through X were evaluated in a newsprint application to determine if silicas of the instant invention will improve the printability of newsprint. Data of silica-filled newsprint is listed in Table VII.

TABLE VII

| NEWSPRINT EVALUATION OF SILICAS OF EXAMPLES I THROUGH X | | | | | | |
|---|---|---|---|---|---|---|
| Example No. | % Filler | Basis Weight | Caliper (mils) | TAPPI Brightness | TAPPI Opacity | S/T* at 2 g/m² Ink | S/T* % Reduction |
| Unfilled | None | 32.2 | 3.3 | 60.0 | 86.1 | 13.8 | — |
| I | 2 | 32.4 | 3.3 | 60.3 | 86.2 | 8.3 | 40 |
|  | 4 | 32.8 | 3.3 | 60.5 | 86.3 | 5.0 | 64 |

TABLE VII-continued
NEWSPRINT EVALUATION OF SILICAS OF EXAMPLES I THROUGH X

| Example No. | % Filler | Basis Weight | Caliper (mils) | TAPPI Brightness | TAPPI Opacity | S/T* at 2 g/m² Ink | S/T* % Reduction |
|---|---|---|---|---|---|---|---|
| II | 2 | 31.9 | 3.3 | 60.5 | 86.3 | 8.6 | 38 |
|  | 4 | 32.2 | 3.3 | 60.8 | 86.4 | 5.3 | 61 |
| III | 2 | 31.5 | 3.2 | 60.7 | 86.3 | 8.1 | 41 |
|  | 4 | 31.7 | 3.2 | 61.3 | 86.4 | 4.7 | 66 |
| IV | 2 | 31.7 | 3.2 | 60.7 | 86.5 | 7.8 | 44 |
|  | 4 | 32.2 | 3.3 | 61.3 | 86.8 | 4.4 | 68 |
| V | 2 | 30.8 | 3.2 | 60.8 | 86.7 | 7.5 | 46 |
|  | 4 | 32.7 | 3.3 | 61.5 | 87.2 | 4.0 | 71 |
| VI | 2 | 31.9 | 3.2 | 60.4 | 86.2 | 8.4 | 39 |
|  | 4 | 32.3 | 3.3 | 60.6 | 86.3 | 5.3 | 62 |
| VII | 2 | 32.2 | 3.3 | 60.5 | 86.4 | 7.4 | 47 |
|  | 4 | 32.5 | 3.3 | 60.9 | 86.5 | 3.9 | 72 |
| VIII | 2 | 31.8 | 3.2 | 60.7 | 86.4 | 7.5 | 46 |
|  | 4 | 31.9 | 3.2 | 61.4 | 86.6 | 4.0 | 71 |
| IX | 2 | 32.0 | 3.2 | 60.9 | 86.7 | 7.6 | 45 |
|  | 4 | 32.3 | 3.3 | 61.5 | 87.2 | 4.2 | 70 |
| X | 2 | 32.0 | 3.2 | 60.9 | 86.5 | 8.4 | 39 |
|  | 4 | 32.0 | 3.2 | 61.5 | 86.8 | 5.1 | 63 |

*S/T = Strike Through

Examination of data in Table VII reveals that silicas of the instant invention increase the brightness, opacity, and print quality of the newsprint. It is clear that silicas of the instant invention when used as fillers increase the strike-through reduction. This is a beneficial property to have for improving the printing properties of newsprint. Thus, silicas when incorporated into the fibers of newsprint result in increased strike-through reduction, brightness, and opacity.

Increase in the brightness and opacity of the newsprint may be attributed to changes in the light scattering properties and increase in surface area which result from the addition of silicas of Examples I through X to the newsprint.

Brightness is increased in the blue region of the spectrum. The result is a whiter, brighter newsprint which has greater contrast with the print.

The combination of reduced migration of the ink vehicle, increased opacity and brightness increases the contrast ratio of printed and unprinted pages and results in sharper half tones of better print quality.

Experiments have indicated that silicas are bonded to the fibrils and distributed through the capillaries between fibrils. In essence, a silica pigment-fiber complex is formed which has significantly different physical and chemical properties from the original fiber.

The following test procedures were used in evaluating the newsprint properties of silicas pigment:

The unfilled furnish was 65 percent groundwood, 35 percent kraft, 0.0002 percent crystal violet, and sufficient alum to adjust the pH to 4.5.

Handsheets containing ash levels of 2 and 4 percent were formed in an 8-in. sheet mould equipped with an 80-mesh wire. The sheets were pressed in a Williams press and airdried overnight in 8-in. by 8-in. drying frams at 73° F. and 50 percent R.H. The sheets were calendered to a caliper of 0.0032 in. and a Bausch and Lomb gloss of about 12 percent.

Optical Testing of the Handsheets

The sheets were evaluated for brightness and opacity according to TAPPI Standards T452 m-58 and T425 m-60 using the Standard Brightness Tester and a B & L Opacimeter.

Physical Testing of the Handsheets

Printing tests were made at standard conditions of temperature and humidity on a Universal No. 1 Vandercook proof press using a standard newsprint ink and a newsprint plate mounted type high. The plate consisted of a series of half tones and a solid area (3½ in. by 3 in.) which was used to measure the print response. Prints were made with 4 mils impression by press bed adjustment and the ink pick-up determined by weighing the sheets before and after printing.

The printing evaluations were made at an ink pick-up equivalent to 2.0 g./m.² for the solid portion; the ink pick-up for the solid area in proportion to the whole print was predetermined by experiment. Although 1.75 ml. of ink applied to the press distribution system produced an ink pick-up near 2.0 g./m.², slight variations in ink pick-up necessitated printing each ash level at three ink levels (1.5, 1.75, 2.0 ml.). The printing value at exactly 2.0 g./m.² was graphically obtained by plotting print values against the actual ink pick-up. Likewise, the ash content varied somewhat so it was necessary to print sheets containing about 2 and 4 percent ash so that comparative values at a given ash content could be obtained by plotting print response against ash content.

Printed sheets were allowed to condition overnight at 73° F. and 50 percent R.H. (relative humidity).

The printing intensity and strike-through were evaluated by the Standard Brightness Tester at 457 mµ and determined in accordance with Larocque's equation:

$$\text{percent printing quality} = 100 - \frac{\text{reflectance (printed)}}{\text{reflectance (unprinted)}} (100)$$

The printed side was used to determine printing quality or color intensity and the reverse or unprinted side for determining strike-through or the degree of ink penetration.

Detergent Compositions

Typical home-laundry detergents consist of the following ingredients:

| Ingredient | Percent, by Weight |
|---|---|
| Sodium Tripolyphosphate | 12–50 |
| Surface Active Agents | 10–20 |

| Ingredient | Percent, by Weight |
|---|---|
| Liquid Sodium Silicate | 5-8 |
| Soil Redeposition Agents | 0.5-1.5 |
| Fluorescent Dyes | 0.05-1 |
| Water | 2-12 |
| Sodium Sulfate | Balance |

Surface active agents mainly consist of anionic linear alkyl benzene sulfonate (LAS) and non-ionic alcohol based ethoxylates (AEO). Surfactant is needed in detergent to extend the functional performance of a detergent builder.

Non-ionic surfactants are added at a level of 4-6% (typical non-ionic surfactants currently being used are Shell's Neodol 25-7 and 45-11) to the other ingredients of detergent compositions. The resulting slurry is spray dried. Non-ionic surfactants contain small fractions of short-chain molecules call "light ends." During the spray drying step, the "light ends" do not incorporate into the finished detergent bead and go out of the dryer exhaust and result in a white cloud referred to as "plume."

Detergent producers are anxious to cut down this "plume" and several mechanical advances have been made to scrub the stack gases but scrubbing process is not 100% effective. Also, the equipment required to clean the stack gases is very expensive.

We have found an inexpensive solution to the problem in which silicas of the present invention can be used to convert the liquid non-ionic surfactants to dry free flowing particulate form so that dried-up surfactant can be post added to the spray dried detergent formulation. Thus, precipitated silica pigments of the instant invention are useful for drying-up non-ionic surfactants in the free flowing form. Thus, silica pigments can be used in the detergent compositions to solve an air pollution problem called "pluming."

Neodol 25-9 surfactant (manufactured by Shell Chemical Company) was dried up by using silica pigments as the carriers or adsorbents. The maximum amount of Neodol that can be dried up on silica is listed in Table VIII.

TABLE VIII

DRYING-UP NEODOL 25-9 ON PRECIPITATED SILICA PIGMENTS

| Silica of Example No. | Flow Time (seconds) | % Active Surfactant |
|---|---|---|
| I* | 36 | 61.2 |
| II | 24 | 65.9 |
| III | 15 | 70.0 |
| IV | 17 | 70.0 |
| V | 18 | 70.9 |
| VI* | 34 | 62.1 |
| VII | 21 | 70.4 |
| VIII | 17 | 71.2 |
| IX | 20 | 69.0 |
| X | 25 | 67.0 |

*Controls

From data in Table VIII above it is clear that silicas of Examples II through V and Examples VII through X exhibit superior flow properties and drying capacity when compared with the corresponding control silicas of Examples I and VI.

Thus, the method of drying up non-ionic surfactants results in superior free flowing surfactant powders. These surfactant powders can be efficiently used by post-adding to detergent compositions. Thus, silicas of the instant invention are useful in detergent compositions and these silica pigments impart superior properties which help in solving an important air pollution problem. Other prior art silicas may be useful, but all such silicas are either very expensive or not efficient enough to be used in detergent compositions.

Pharmaceutical and Cosmetic Compositions

As a vehicle for liquid pharmaceutical preparations, polyols are used extensively and these polyols offer many unique advantages for syrups, elixirs, and other liquid pharmaceutical and cosmetic formaulations.

Sorbitol and glycerine are widely used as humectants in pharmaceutical and cosmetic preparations. Sorbitol is commercially available from ICI, U.S.A. in a 70% solution under the trademark "Sorbo." Sorbo is a sugar alcohol, $C_6H_8(OH)_6$ which occurs in nature as a nutritive ingredient of many fruits and berries. Sorbitol, chemically is a hexahydric member of the polyhydric alcohol or polyol family, of which glycerine is the trihydric member.

The silica pigments of the instant invention can be efficiently used in a variety of cosmetic products where a thickener, suspending agent, emulsion stabilizer, emulsification aid, binder, or a viscosity building agent is required.

The efficiency with which silica pigments of the instant invention can be used in drying up humectants can be seen by examining data of Table IX. For use in cosmetics, the silica pigments of Examples I through V were air milled using a fluid energy mill and then incorporated in various humectants.

Humectant A: This solution was prepared by mixing 45 parts of sorbitol solution with 15 parts of glycerine.

Humectant B: This solution was prepared by mixing 30 parts of sorbitol solution with 20 parts of glycerine.

Humectant C: This solution was prepared by mixing 20 parts of sorbitol with 30 parts of glycerine.

Humectant D: This solution was prepared by mixing 15 parts of sorbitol with 30 parts of glycerine.

TABLE IX

| | % ACTIVE HUMECTANT /100 g SILICA | | | |
|---|---|---|---|---|
| Silica of Example No. | Humectant A | Humectant B | Humectant C | Humectant D |
| I | 157 | 165 | 175 | 180 |
| II | 230 | 280 | 250 | 220 |
| III | 250 | 300 | 320 | 250 |
| IV | 220 | 250 | 210 | 280 |
| V | 210 | 200 | 220 | 200 |

The silica pigments of the instant invention exhibit superior viscosity building and carrying capacity than the control silica of Example I.

The viscosity building data of silicas from Example I through V in Humectant A is given in Table X.

TABLE X

VISOCITY BULIDING PROPERTIES IN HUMECTANT A

| Silica From Example No. | Percent Loading of Silica in Humectant A | | |
|---|---|---|---|
| | 2.5% | 5.0% | 10% |
| I | 350 CPS | 400 CPS | 850 CPS |
| II | 400 CPS | 750 CPS | 2000 CPS |
| III | 350 CPS | 500 CPS | 2850 CPS |
| IV | 325 CPS | 450 CPS | 1200 CPS |
| V | 338 CPS | 500 CPS | 2250 CPS |

The viscosity data was run by using Brookfield Viscometer.

Paint Coating Composition

The silica pigments of the instant invention were air milled using fluid energy mill and then incorporated in a paint system for reduction in gloss of a paint system.

In order to provide protection and to produce a pleasing appearance, a variety of surfaces, such as wood, metal, fabric, paper, or plastics, are coated with clear flatting compositions containing dispered or suspended particles of a flatting agent which reduces the gloss or sheen of the coating and the coated substrate, preferably without substantially reducing the transparency of the flat coating. For example, wood finishes which serve to protect the surface against abrasion and strain, yet do not conceal the beauty of the grain, are made to simulate desirable hand-rubbed finishes by incorporating flatting agents therein which normally are dispersed fine particles of such materials as silicas. The best effects are obtained with silicas of uniform particle size down to the submicron range. Small size and uniformity are necessary to achievwe a smooth coating without white specks or without a graying effect which would detract from the appearance of the coating.

For paint flatting application, 10 grams of silica (which was air milled) of the instant invention was mixed with 350 grams of the nitrocellulose lacquer (comforming to Military specification MIL-L-10287A—amendment 2, Type II, of issue 27, August 1959) and mixed for 3 minutes using the low speed setting of the Hamilton-Beach #30 mixmaster. The lacquer containing dispersed silica was tested for Hegman fineness of grind (5.50) and cleanliness of grind.

The lacquer containing dispersed silica from Examples II through V was mixed with no lacquer and additional lacquer to prepare stock solution containing 10%, 3.5%, and 1.75% by weight of vehicle solids. A drawdown of various stock solutions (containing 10%, 3.5%, and 1.75% silica is lacquer) was made on carrara glass using a 34 wire coatings application rod. Carrara glass drawdowns were allowed to dry for 45 minutes under dust-free conditions. Using the above method, drawdowns were also made from stock solutions containing the silica developed via the prior art processes of Example I.

Using the Gardner multi-angle gloss meter, the gloss and sheen values of the various drawdowns were measured at 60° and 85°, respectively. These values were compared with measured values obtained when a prior art silica was dispersed in the lacquer.

Silicas of the present invention result in cleaner Hegman grinds and exhibit better clarity when dispersed in the lacquer. The better clarity is attributed to the fact that the silicas of the present invention are of uniform particle sizes and favorable structures.

Flatting data listed in Table XI suggests that the novel silicas of the present invention exhibit lower gloss and sheen values than the control, Example I. Lower gloss and sheen values are preferred and advantageous for paint flatting applications.

TABLE XI

| Silica From | PAINT FLATTING EVALUATION | | | | | |
|---|---|---|---|---|---|---|
| | 60° Gloss | | | 85° Sheen | | |
| Example No. | 10% | 3.5% | 1.75% | 10% | 3.5% | 1.75% |
| I | 10 | 38 | 54 | 37 | 72 | 82 |
| II | 8 | 28 | 27 | 26 | 59 | 71 |
| III | 6 | 20 | 31 | 20 | 30 | 51 |
| IV | 5 | 22 | 29 | 18 | 29 | 57 |
| V | 7 | 28 | 31 | 15 | 17 | 39 |

Examining data of Table XI, it is clear that post-treated silicas, Example II through V, exhibit superior properties than the control of Example I (no post-conditioning).

Dentifrice Composition

The silica pigments of the instant invention can be efficiently used as thickening agent in dentifrices. Where a controlled refractive index thickener is required, this property can be controlled by the addition of small amount of an adduct material as illustrated in Examples VI through X. Controlled refractive index silicas (see Example VII through X) exhibit superior thickening properties in a clear gel toothpaste than the control of Example VI.

If the pigments of the invention are used in toothpaste compositions, the dentifrice (if in the form of a paste) may contain humectant materials and binders to give the dentifrice a smooth texture and good flowability. Glycerine, sorbitol, corn syrup, glucose, and the like may be used as carriers. Examples of binders include gum tragacanth, sodium carboxymethylcellulose, and the like. The above materials, as well as the specific formulation of the toothpaste, are well known in the art and are disclosed, for example, in U.S. Pat. Nos. 2,994,642 and 3,538,230 and numerous publications.

As discussed above, the unique silicas of the invention may be advantageously employed as thickening and polishing agents in toothpaste compositions. This is truly remarkable inasmuch as precipitated silicas of the prior art cannot be so employed. If the products of the invention are used in toothpaste compositions, and as known in the art, the dentifrice may contain, e.g., humectant minerals and binders to give the dentifrice a smooth texture and good flowability. A detailed disclosure of dentifrice formulations is given in U.S. Pat. No. 3,729,961.

In this regard, dentifrice formulations have been produced, ranging from liquids and powders to the highly popular pastes or dental creams. Dental creams are the more difficult to compound successfully in that they require careful balancing of polishing agent, humectant, water, binder, preservatives, detergents, flavoring, sweeteners, and therapeutic agents to produce a smooth homogeneous paste.

Most modern dental cream formulations use one of several phosphate materials as the polishing agent. Examples of the phosphate polishing agents are dicalcium phosphate, anhydrous dicalcium phosphate, tricalcium phosphate, thermally converted dicalcium phosphate, and insoluble sodium metaphosphate. The amount of phosphate materials added to the dental formulations will range between about 5 percent and 60 percent by weight.

The most widely used humectants in toothpaste are glycerine and sorbitol. Propylene glycol is also used in small amounts and to a very limited extent. The primary function of humectant as part of the liquid phase is to retain moisture which provides good texture and maintains an attractive glossy appearance when the paste is exposed to air.

The binder employed therein is to prevent separation of the liquid and solid phases. The most conventionally used binders are the seaweed colloids and synthetic derivatives of cellulose, specifically carragcenan and sodium carboxymethyl cellulose. Others, such as gums, have been used. Combinations of these binders have also been employed.

Since the natural and synthetic water dispersions of organic binders are subjected to microbial or mold attack, a relatively small amount of preservatives is added to the paste. Examples of preservatives used in the industry are the esters of parahydroxyl benzoates.

The function of the detergents within the dental formulation is to provide greater cleansing action due to the lowering of the surface tension and the sudsing action in the mouth. Among detergents used are sodium N-lauryl sarcosinate, sodium lauryl sulfate, sulfoculaurate, sodium alkyl sulfoacetate, and sodium dioctyl sulfosuccinate.

Since toothpaste flavoring probably represents the greatest single factor in consumer acceptance, great care has been employed in selecting balanced blends of different essential oils. These are rarely, if ever, used alone. Combinations of principal flavors are wintergreen, peppermint, and sassafras, and are used with secondary oils such as pimento, clove, and anise.

Saccharin and sodium cyclamate are widely used to improve taste and enhance the flavor qualities of the toothpaste. The synthetic sweeteners may be used in combination to obtain optimum sweetness and absence of after-taste. Their desirable properties are obtained at very low concentrations and consequently they have negligible influence on the toothpaste consistency.

Since water is such a common element, it is important in obtaining stable toothpaste formulations to employ substantially pure water therein. It is common practice to demineralize the water that is employed.

The therapeutic agents within the dental creams are to prevent decay of the tooth and are commonly in the form of stannous fluorides and sodium fluoride material.

Difficulties have been encountered in using combinations of the above materials in modern dentifrice formulations. Specific scavenging of the fluoride ions by the phosphate and calcium containing polishing agents have been experienced. Thus, in formulating a dentifrice composition, a plishing agent must be selected to provide excellent polishing properties and have a very high degree of compatibility with the fluoride system and an particular should not scavenge the fluoride ion.

The silica pigments when prepared by the improved process disclosed in the instant invention are suitable for use in dentifrices as a thickener. While the prior art silicas are not suitable due to controlled physical-chemical properties and due to control of refractive index, the silicas of the instant invention are useful thickeners in clear-gel and opaque dentifrices.

It is disclosed in the literature that conventional synthetic precipitated silicas are unsuitable as polishing and abrasive agents in toothpaste compositions. See German Pat. No. 974,958; French Pat. No. 1,130,627; British Pat. No. 995,351; Swiss Pat. No. 280,671; and U.S. Pat. No. 3,250,680. In this regard, it is disclosed in U.S. Pat. No. 3,538,230 that known amorphous silicas, such as precipitated silicas, pyrogenic silicas, and aerogels, are unsuitable for dentifrice use because they show substantially no cleaning ability on human teeth because of their initial small particle size and because of the ease in which they break down into small particle sizes which result in poor cleaning ability.

Further, and in more detail, conventional silicas and amorphous precipitated alumino silicates cannot be used for a clear-gel toothpaste because of their high refractive index (1.55) and because they lack the needed thickening, polishing characteristics when added to the toothpaste base composition. Clear-gel toothpaste contains a high percentage of abrasive and polishing agent in the toothpaste formula. The major function of the abrasive and polishing agent is to remove stains, food debris, and bacterial plaque from the human tooth surface. Ideally the polishing agent should provide a maximum cleaning action at acceptable abrasion levels and must be compatible at high loadings of 15% up to 50% with other toothpaste formula ingredients.

In an excellent chapter on Dentifrices in Sagarin's book, *Cosmetics: Science & Technology,* Gershon and Morton Pader have reviewed several dentifrice formulations. We have found that controlled refractive index silicas of Examples VII through X are useful thickeners when formulated in a clear-gel dentifrice formulation No. 8 listed on page 500 of Sagarin's book. The dentifrice formulation No. 8 listed on page 500 consists of the following ingredients:

| | |
|---|---|
| Dehydrated silica gel | 14.00% |
| Silica aerogel | 7.50% |
| Sodium carboxymethylcellulose | 0.60% |
| Sorbitol solution, 70% | 67.82% |
| Glycerol | 5.74% |
| Sodium lauryl sulfate | 1.26% |
| Color, flavor | 2.77% |
| Sodium hydroxide solution, 30% | 0.31% |

In the above formulation, silica aerogel was substituted by silicas of the instant invention and acceptable thickening properties were imparted by these unique silicas of Examples VII through X.

Silicas of Examples II through V and VII through X can also be used as efficient thickeners in opaque dentifrices.

What is claimed is:

1. A dentifrice including, as a thickening and polishing agent, a finely divided, amorphous, precipitated silicon dioxide having the combined properties of a structure index of less than 505 and an oil absorption of greater than 190 cc/100 grams; said silicon dioxide comprising not less than 90% $SiO_2$ and including a metal cation incorporated therein, said metal cation serving to control the refractive index of said silicon dioxide such that said refractive index is not less than 1.45 and serving to control the surface area of said silicon dioxide such that said surface area is not less than 153 $m^2$/gram, said metal cation being selected from the group consisting of aluminum, magnesium, zinc, and calcium.

2. A dentifrice including, as a thickening and polishing agent, a finely divided, amorphous, precipitated silicon dioxide having a wet cake moisture content of from between about 79.8 to 83.5%; a structure index of from between about 359 to 505; an oil absorption of from between about 190 to 202 cc/100 grams; a void volume of from between about 3.55 to 4.14 cc Hg/gram $SiO_2$; a BET surface area of from between about 120 to 153 $m^2$/gram; and a percent friability of up to about 98%.

3. A dentifrice including, as a thickening and polishing agent, a finely divided, amorphous, precipitated silicon dioxide having a wet cake moisture content of from between about 77.9 to 83.2%; a structure index of from between about 365 to 495; an oil absorption of from between about 193 to 212 cc/100 grams; a void volume of from between about 3.19 to 4.40 cc Hg/gram $SiO_2$; a BET surface area of from between about 153 to 220 $m^2$/gram; and a percent friability of up to about 93%; said silicon dioxide comprising at least 90% $SiO_2$ and having incorporated therewith a metal cation selected from the group consisting of aluminum, magnesium, zinc, and calcium to thereby control the surface area thereof and to increase the refractive index thereof to a value of at least 1.45.

4. A dentifrice composition according to claim 1 in a form of a toothpaste which comprises said thickening and polishing agent together with humectants, binders, preservatives, detergents, flavoring agents, sweeteners and therapeutic agents.

5. A toothpaste according to claim 4 wherein said humectant is selected from the group consisting of glycerine, sorbitol and mixtures thereof, and wherein said binder is selected from the group consisting of seaweed colloids, synthetic derivatives of cellulose, gums and mixtures thereof.

6. A dentifrice composition according to claim 2 in a form of a toothpaste which comprises said thickening and polishing agent together with humectants, binders, preservatives, detergents, flavoring agents, sweeteners and therapeutic agents.

7. A toothpaste according to claim 6 wherein said humectant is selected from the group consisting of glycerine, sorbitol and mixtures thereof, and wherein said binder is selected from the group consiting of seaweed colloids, synthetic derivatives of cellulose, gums and mixtures thereof.

8. A dentifrice composition according to claim 3 in a form of a toothpaste which comprises said thickening and polishing agent together with humectants, binders, preservatives, detergents, flavoring agents, sweeteners and therapeutic agents.

9. A toothpaste according to claim 8 wherein said humectant is selected from the group consisting of glycerine, sorbitol and mixtures thereof, and wherein said binder is selected from the group consisting of seaweed colloids, synthetic derivatives of cellulose, gums and mixtures thereof.

10. A clear gel toothpaste composition containing humectants and binders in the liquid phase, and thickening and polishing agents, said composition including, as a thickening and polishing agent, a finely divided, amorphous, precipitated silicon dioxide having the combined properties of a structure index of less than 505 and an oil absorption of greater than 190 cc/100 grams; said silicon dioxide comprising not less than 90% $SiO_2$ and including a metal cation incorporated therein, said metal cation serving to control the refractive index of said silicon dioxide such that said refractive index is not less than 1.45 and serving to control the surface area of said silicon dioxide such that said surface area is not less than 153 $m^2$/gram, said metal cation being selected from the group consisting of aluminum, magnesium, zinc, and calcium; wherein the refractive index of said liquid phase is substantially the same as said silicon dioxide.

11. A clear gel toothpaste composition containing humectants and binders in the liquid phase, and thickening and polishing agents, said composition including, as a thickening and polishing agent, a finely divided, amorphous, precipitated silicon dioxide having a wet cake moisture content of from between about 79.8 to 83.5%; a structure index of from between about 359 to 505; an oil absorption of from between about 190 to 202 cc/100 grams; a void volume of from between about 3.55 to 4.14 cc Hg/gram $SiO_2$; a BET surface area of from between about 120 to 153 $m^2$/gram; and a percent friability of up to about 98%; wherein the refractive index of said liquid phase is substantially the same as said silicon dioxide.

12. A clear get toothpaste composition containing humectants and binders in the liquid phase, and thickening and polishing agents, said composition including, as a thickening and polishing agent, a finely divided, amorphous, precipitated silicon dioxide having a wet cake moisture content of from between about 77.9 to 83.2%; a structure index of from between about 365 to 495; an oil absorption of from between about 193 to 212 cc/100 grams; a void volume of from between about 3.19 to 4.40 cc Hg/gram $SiO_2$; a BET surface area of from between about 153 to 220 $m^2$/gram; and a percent friability of up to about 93%; said silicon dioxide comprising at least 90% $SiO_2$ and having incorporated therewith a metal cation selected from the group consisting of aluminum, magnesium, zinc, and calcium to thereby control the surface area thereof and to increase the refractive index thereof to a value of at least 1.45; wherein the refractive index of said liquid phase is substantially the same as said silicon dioxide.

* * * * *

UNITED STATES PATENT AND TRADEMARK OFFICE
CERTIFICATE OF CORRECTION

PATENT NO. : 4,336,245
DATED : June 22, 1982
INVENTOR(S) : Satish K. Wason

It is certified that error appears in the above—identified patent and that said Letters Patent is hereby corrected as shown below:

First page at Part [63] and Column 1, line 8, after "abandoned", the following phrase should be inserted: -- ; which is a continuation-in-part of Serial No. 286,655, filed September 6, 1972, now issued as Patent No. 3,893,840 --.

Column 10, line 5, "hearin" should be -- herein --.

Column 15, line 9, "experiment" should be -- experiments --.

Column 24, line 12, "formaulations" should be -- formulations --.
line 38, in Humectant C, "30 parts of glycerine" should be -- 20 parts of glycerine --.
line 57, "VISOCITY" should be -- VISCOSITY --.

Column 25, line 21, "achievwe" should be -- achieve --.
line 39, "is lacquer" should be -- in lacquer --.
line 40, "34 wire" should be -- #34 wire --.

Column 27, line 6, "carragcenan" should be -- carrageenan --.
line 48, "plishing" should be -- polishing --.
line 51, "an particular" should be -- in particular --.

Column 30, line 31, "clear get" should be -- clear gel --.

Signed and Sealed this

Eleventh Day of October 1983

[SEAL]

Attest:

GERALD J. MOSSINGHOFF

Attesting Officer  Commissioner of Patents and Trademarks